United States Patent [19]

Robinson et al.

[11] Patent Number: 5,409,917

[45] Date of Patent: Apr. 25, 1995

[54] TOPICAL TREATMENT OF ACNE WITH CEPHALOSPORINS

[75] Inventors: Howard N. Robinson, Lutherville; Neil F. Martin, Potomac, both of Md.

[73] Assignees: Marvin S. Towsend, Towson; Leonard Bloom, Rockville, both of Md.; a part interest to each

[21] Appl. No.: 126,799

[22] Filed: Sep. 24, 1993

Related U.S. Application Data

[63] Continuation-in-part of Ser. No. 883,914, May 12, 1992, Pat. No. 5,260,292, which is a continuation-in-part of Ser. No. 664,795, Mar. 5, 1991, abandoned.

[51] Int. Cl.$^6$ ............................................ A61K 31/545
[52] U.S. Cl. ..................................... 514/200; 514/201; 514/202; 514/203; 514/204; 514/205; 514/206; 514/207; 514/208; 514/209; 514/159; 514/557; 514/714; 514/725; 424/703; 424/401
[58] Field of Search ........................... 514/200–210, 514/886, 887, 159, 714, 557, 725; 424/703, 401

[56] References Cited

U.S. PATENT DOCUMENTS 4,444,755  4/1984  Horrobin ........................... 424/145

FOREIGN PATENT DOCUMENTS 0005348  11/1979  European Pat. Off. .

OTHER PUBLICATIONS

Fisher, Current Contact News, 25, 1980, p. 474.
Frank, Postgrad. Med., 61, (6), 1977.

*Primary Examiner*—Gollamudi S. Kishore
*Attorney, Agent, or Firm*—Leonard Bloom; Marvin S. Towsend

[57] ABSTRACT

A method and composition for topically treating acne and acneiform dermal disorders includes applying an amount of a cephalosporin antibiotic effective to treat the acne and acneiform dermal disorders. The antibiotic is blended with a carrier suitable for topical application to dermal tissues. The carrier is selected from the group consisting of an aqueous liquid, an alcohol base, a water soluble gel, a lotion, an ointment, a nonaqueous liquid base, a mineral oil base, a blend of mineral oil and petrolatum, liposomes, a time-release patch, and a liquid-absorbed wipe. The cephalosporin can also be combined with benzoyl peroxide in a gel carrier.

14 Claims, No Drawings

TOPICAL TREATMENT OF ACNE WITH CEPHALOSPORINS

CROSS-REFERENCE TO RELATED APPLICATION

The present application is a continuation-in-part application of Ser. No. 07/883,914, filed May 12, 1992, entitled TOPICAL TREATMENT OF ACNE WITH AMINOPENICILLINS, now U.S. Pat. No. 5,260,292. Patent application Ser. No. 07/883,914, filed May 12, 1992 is a file wrapper continuation-in-part application of parent application Ser. No. 07/664,795, filed Mar. 5, 1991, by the same inventors, entitled TOPICAL TREATMENT OF ACNE, now abandoned.

FIELD OF THE INVENTION

The present invention relates to the field of treating the skin condition known as acne. More specifically, the present invention is concerned with the prophylactic or therapeutic topical treatment acne. Even more specifically, the present invention is concerned with the topical treatment of acneiform dermal conditions such as acne vulgaris, preadolescent acne, acne rosacea (now known as rosacea), premenstrual acne, acne venenata, acne cosmetica, pomade acne, acne detergicans, acne cosmetica, acne excoriee, gram negative acne, steroid acne, acne conglobata, or nodulocystic acne. The present invention can also be used for topically treating certain types of dermatitis, e. g. perioral dermatitis, seborrheic dermatitis, gram negative folliculitis, sebaceous gland dysfunction, hidradenitis suppurativa, pseudofolliculitis barbae, or folliculitis.

BACKGROUND OF THE INVENTION

Acne vulgaris is a common disease which afflicts approximately 90% of all teenagers, and, not uncommonly, affects men and women in their twenties or thirties or may persist in adults for many years. Acne vulgaris most commonly occurs on oily areas of the skin with high sebaceous gland concentration. The areas of high sebaceous gland concentration are the face, ears, retroauricular areas (e. g. behind the ears), chest, back, and occasionally the neck and upper arms.

Acneiform eruptions can occur wherever there is a pilosebaceous unit or sebaceous follicle which does include the entire surface of the skin.

The basic lesion in acne is the comedo commonly known as the blackhead. The comedo is created by retention of layers of dead skin known as keratin in the lining of the follicles. In addition to hyperkeratosis (which is thickening or retentative layering of keratin), there is an accumulation of sebum which is the lipid-laden product of the sebaceous gland. The cells of the sebaceous glands in which sebum originates are the sebocytes. The combination of the keratin and the sebum produces a plugging of the mouth or opening of the follicular canal, and papules are formed by inflammation around the comedones (plural of comedo). Depending upon the degree of inflammation, pustules, cysts, nodules, granulomatous reactions, scars, and keloids may develop.

Most typical forms of mild acne vulgaris demonstrate the predominance of comedones with the occasional pustules. Pustules and papules predominate in more severe cases. These can heal with scars forming; that is, fibrosis of the lesions occurs that are deep and penetrating. In moderately active cases, larger cystic lesions can develop.

Acne vulgaris can appear in many clinical varieties. The mildest case manifests comedones on oily skin and is called acne comedo.

Papular acne is another variety of acne which has many inflammatory papules. This form of acne is common in adolescent skin, but it can be seen in all ages. The papular inflammatory form of acne can progress to an indurated, deeper, and destructive form known as acne indurata. These lesions can produce severe scarring and can be quite deep seated and destructive.

Steroid acne vulgaris can occur when oral corticosteroids or topical steroids are used and occurs as inflammatory follicular papules. When oral corticosteroids are ingested, the inflammatory papules are usually sudden in appearance and can cover the chest, back, arm, and face. When topical corticosteroids are used for more than two weeks, a localized inflammatory papular response can develop which can proceed to a granulomatous chronic reaction known as steroid acne rosacea.

Premenstrual acne can occur in a large number of menstruating women as a papular and pustular acne vulgaris, approximately one week prior to menstruation. There is a body of evidence that implicates a surge in progesterone as the mediator of premenstrual acne.

Preadolescent acne is divided into neonatal, infantile, and childhood forms of acne. The neonatal form is limited to the first few weeks of life. It usually develops a couple of days after birth. It more commonly afflicts males and reveals transient facial papules and pustules which can clear spontaneously in a few days or weeks. The stimulation of neonatal sebaceous glands by circulating maternal progesterone appears to be the cause.

If the acne persists beyond the first month of life, the acne is called infantile acne and can extend into childhood, adolescence, and adult life. The childhood acne can result from a persistent infantile acne or can develop de novo after age two. This form of acne is uncommon, but it has more of a male predilection. It is characterized by comedones commonly in groups, papules, pustules, and, rarely, cysts. This condition can extend from a few weeks to several years and can develop into pubertal acne.

Acne venenata is by definition a comedonal or papular acne which occurs after exposure to chlorinated hydrocarbons (chloracne), cutting oils, petroleum oil, coal tar, and pitches.

Acne cosmetica is a persistent low grade comedonal and/or papular and pustular acne that occurs usually on the chin and cheeks of adult women due to oil-based cosmetics, i. e. foundations, facial creams, and sunscreens.

Pomade acne is a type of acne cosmetica which appears to occur almost exclusively in black persons who apply grease and oil to scalp hair and the face as a grooming aid. The lesions are predominately comedonal acne and can develop into inflammatory acne papules, depending upon the chronicity of the pomade use.

Acne detergicans occurs as a type of comedonal acne in patients who use oil-based cleansing soaps. Acne excoriee, also known as pickers acne, starts out as mild form of papular or comedonal acne which is manipulated or picked and causes further inflammation, more papules, and sometimes scars, pitting, and atrophy of the skin.

Gram negative acne, sometimes called gram negative folliculitis when it extends to the neck, arms, legs, and trunk, is a form of an inflammatory papular, follicular, and pustular response to gram negative organisms including Enterobacter, Klebsiella, Escherichia, Proteus, Serratia, and Pseudomonas. The most characteristic lesion on the face is superficial pustules, or papulo-pustules (which is a combination of a papule and pustule). The face can show diffuse erythema and inflammation surrounding these pustules and juicy papules or papulo-pustules.

The gram negative acne is usually highly resistant and usually occurs in patients who have bad inflammatory papular acne for long periods or who have been treated with long term oral administration of antibiotics such as tetracycline, erythromycin, or minocycline or topical antibiotics such as topical clindamycin or topical erythromycin. Subsequent to the oral administration tetracycline or erythromycin, oral administration of amoxicillin, ampicillin, and trimethoprin-sulfomethoxazole has been shown to be effective in treating this disease. (Poli, F., Prost, C., Revuz, J., Gram-negative Folliculitis, Ann. Dermatol. Venereol., 115:797–800, 1988). In another reference, Marks, R. and Ellis, J., "Comparative effectiveness of tetracycline and ampicillin in rosacea", *Lancet* 1971 vol 2 pages 1049–1052, there is a disclosure that ampicillin has been used orally for treatment of rosacea. More specifically, orally administered ampicillin was compared with orally administered tetracycline in the treatment of rosacea.

Acne rosacea is an inflammatory eruption that is chronic and occurs on the face, especially on the nose as well as the scalp and neck, in some instances. It is manifested by erythema, pustules, papules, telangieclasia (which is dilation of superficial capillaries), and hypertrophy of sebaceous glands. The middle portions of the face are most frequently involved. The eyes and eyelids are not uncommonly involved and can produce inflammation and infection of the conjunctiva, eyelids, and hypertrophy of the meibomian glands. Acne rosacea is often called simply rosacea and is most common in middle aged women and men. Rosacea can go on to form a granulamatous roscea which is characterized by resistant inflammatory papules which when biopsied reveal noncaseating epithelial cell granulomas.

Pseudofolliculitis barbae is a predominantly male affliction which is characterized by inflammatory papules and pustules on the bearded area of the face most commonly in black persons, but all racial groups can be affected. The mechanism is thought to be an inflammatory response to the end of hair (usually curly beard facial hair) into the skin causing a foreign body inflammatory response.

Folliculitis is an inflammatory reaction around the hair follicle which can be bacterial or nonbacterial in nature. Predominately, folliculitis is caused by gram positive organisms such as Staphylococcus and Streptococcus, and less frequently by gram negative bacteria discussed hereinabove with respect to gram negative folliculitis.

Perioral dermatitis is a common papular inflammatory eruption which is confined around the mouth. It most commonly afflicts women in their early twenties to middle thirties, but it can be seen in adolescents and more mature adults.

Hidradenitis suppurativa is a suppurative (chronic) and cystic disease of apocrine gland regions of the skin, including the axillae and groin.

There is a genetic tendency to acne, in particular acne congoblata which is a deep cystic and sinus forming type of acne. This condition is essentially a deep, aggressive form of cystic acne occurring in the apocrine gland regions. Topical administration of clindamycin has been used to treat this form of cystic acne.

The etiology of acne vulgaris and related disorders as discussed above is not completely known in every detail. However, what is known is that acne, in general, is caused by a plurality of factors. In general, there are four main factors that cause acne: genetics; hormonal activity; bacteria; and the inflammatory response.

Genetics is a prominent component as it is well known that several members of the same family can be affected with moderate to severe scarring acne. The inheritance by some is thought to be autosomal dominant, but this has not been definitively proven. Furthermore, on the molecular level, there has not yet been discovered a gene or group of genes that are responsible for the various forms of acne vulgaris.

Another key factor in the development of acne is hormonal. In adolescence, for example, it is thought that androgens can interact with receptors on the sebaceous glands and cause stimulation of the sebaceous gland to hypertrophy and hence form more sebaceous production of lipids and free fatty acids which distend the follicular canal. More specifically, there is evidence for increased peripheral metabolic conversion of the androgen testosterone to dihydrotestosterone at the level of the skin in acne patients. It is further hypothesized that receptors on the sebaceous gland for the active androgen dihydrotestosterone can exhibit various degrees of sensitivity, and that a heightened sensitivity response may be partially or entirely genetically predetermined.

Another causative factor in acne is the presence of bacteria in the follicular canal. Within the follicular canal are bacteria which are indigenous to the follicular lining. They are anaerobic, gram positive organisms called Propionibacterium acnes. It is interesting to note that they are present in abundance in pathologically affected sites. They are reduced during oral antimicrobial treatment, and their absence from nonhuman animal skin is striking especially since animals do not exhibit acne vulgaris.

Yet another causative factor in acne is the inflammatory response manifested in the skin. More specifically, it is thought that Propionibacterium acnes lives in symbiosis on the keratin lined follicular canal. Propionibacterium acnes ingests the sebum produced from the sebocytes of the sebaceous glands. This nascent sebum is largely lipid in composition and also contains DNA, RNA, proteins, and other cellular components that result from the breakdown of sebocytes themselves. The Propionibacterium acnes which are highly lipophilic, feed on the nascent sebum. It has been shown that Propionibacterium acnes are found only in sebaceous rich areas. If the nutrients increase due to an active and large sebaceous system, then colonization and high growth rates of Propionibacterium acnes will form. It has been shown that the resident bacterial flora will produce biologically active molecules such as histamine, extracellular enzymes, and peptides which may be responsible for the chemotaxis of the inflammatory infiltrate in acne vulgaris. Since the follicular lining in the pilosebaceous unit is intact, it has been theorized that if colonization of Propionibacterium acnes occurs in sufficient numbers, they could produce initiating autogenic molecules that promote the initiating of inflammation. Propionibacterium acnes can produce proteinases, lipase, and hyaluronate lyase all of which may serve as the catalysts or initiators of the inflammatory infiltrate which has been shown to be composed of neutrophils and lymphocytes.

A number of treatments are presently known for treating acne, some more successful than others. Some modes of treatment have been mentioned above. There are two basic ways to administer a therapeutic agent: topical and systemic.

Aside from treatments mentioned above, some additional systemic treatments for acne that are presently employed are: oral tetracycline; oral erythromycin; minocycline; doxycycline; oral trimethoprim-sulfamethoxazole and isotretinoin (ACCUTANE TM).

Those that have been suggested in the past and that are no longer generally employed include: antibacterial vaccines; estrogen therapy; dietary restrictions; and vitamin therapy (e. g. oral ingestion of vitamin A).

Some of the topical treatments that are presently employed are: topical erythromycin, clindamycin, benzoyl peroxide, 2% sulfur, 3% resorcinol, a tetracycline derivative (meclocycline sulfosalicylate 1%), 2% salicylic acid, and tretinoin (Retin-A TM).

Topical treatments that have been suggested in the past and that are no longer generally employed include: x-ray treatment; electric sparks; vitamin therapy; treatment with a plant extract as described in U.S. Pat. No. 4,803,069.

More specifically with respect to the topical use of certain specific antibiotics, a topical solution, ointment, and gel containing erythromycin is used. Also used is a topical solution, gel, and lotion containing clindamycin, and a cream containing meclocycline sulfosalicylate (a tetracycline derivative).

Some of the undesirable side effects of orally administered antibiotics are abdominal cramps, black tongue, cough, diarrhea, fatigue, irritation of the mouth, loss of appetite, nausea, vomiting, fever, hearing loss, jaundice, rash, rectal and vaginal itching, and superinfection.

It is noted that erythromycin is produced by the bacterium *Streptomyces erytheus* and that erythromycin has a chemical structure that is substantially unique to erythromycin and its derivatives. The molecular weight of erythromycin A is 733.92. The empirical formula for erythromycin A is $C_{37}H_{67}NO_{13}$ having a 60.55% carbon content, a 9.20% hydrogen content, a 1.91% nitrogen content, and a 28.34% oxygen content.

Clindamycin has a chemical structure indicated by its chemical name which is methyl 7-chloro-6,7,8-trideoxy-6-[[(1-methyl-4-propyl-2-pyrrolidinyl)carbonyl]amino]-1-thio-L-threo-alpha-D-galacto-octopyranoside. The molecular weight of clindamycin is 424.98. The empirical formula for clindamycin is $C_{18}H_{337}ClN_2O_5S$ having a 50.87% carbon content, a 7.83% hydrogen content, a 8.34% chlorine content, a 6.59% nitrogen content, a 18.82% oxygen content, and a 7.54% sulfur content.

Other topical treatments for acne using antibiotics are described in the following Great Britain patents: neomycin, G. B. Pat. No. 1,054,124; erythromycin, G. B. Pat. No. 1,587,428; and erythromycin derivatives in conjunction with benzoyl peroxide, G. B. Pat. Nos. 2,088,717 and 2,090,135.

Still another topical treatment for acne, more specifically acne vulgaris, includes preparation of a hyaluronic acid derivative which is a bridged conjugate of hyaluronic acid (which is a linear polymer of N-acetyl glucosamine and glucuronic acid units) bonded to a bridging agent (which is cyanogen bromide) which, in turn, is bonded to the amino-nitrogen atom of the aminopenicillin, ampicillin. Thus, with this hyaluronic acid derivative, the amino-nitrogen of the aminopenicillin is no longer in the form of a primary amino group. This hyaluronic acid derivative is disclosed in Great Britain Published Application 2,207,142.

Still other topical treatments for acne using anti-bacterials are described in the following U.S. patents: an azole derivative in conjunction with benzoyl peroxide, U.S. Pat. No. 4,446,145, incorporated herein by reference; and metronidazole in a special gel as described in U.S. Pat. No. 4,837,378, incorporated herein by reference.

It is noted that none of the topical treatments mentioned above disclose the treatment of acne topically with a cephalosporin.

It is recalled that the applicants parent U.S. patent application was filed Mar. 5, 1991. In addition, prior art treatments and proposed treatments for acne have spanned many years and have been published in a large number of publications, some of which are discussed above and some of which are discussed below.

In Kirk-Othmer, Encyclopedia of Chemical Technology, Third Edition, Volume 2, (1978), page 812, there is Table 2 in which it is disclosed that cephalosporin C, N, P were discovered in 1948; cephalothin was discovered in 1962; and cephalexin was discovered in 1967.

In Frank, "Treatment of Acne with Topical Antibiotics", Postgrad. Med., 61(6):92–8, June 1977, there is a disclosure that a number of antibiotics are used in the topical treatment of acne vulgaris. A 2% erythromycin base was used in an alcohol-water vehicle. A 0.5% tetracycline was used in an alcohol-water vehicle which also contained a penetration-enhancing material, n-decyl methyl sulfoxide [$C_{10}SO$]. Clindamycin phosphate was incorporated in an alcohol-water vehicle. Also, 1% clindamycin phosphate was incorporated in a methyl pyrrolidone vehicle.

Also, on page 98, under the subtopic "Penetrant effect of the vehicle" there is a statement that equal parts of alcohol and water (as well as $C_{10}MSO$ and methyl pyrrolidone) have a penetrant effect to penetrate the canal of the sebaceous follicle. There is no mention of any form of a cephalosporin whatsoever. Thus, for fourteen years prior to the Applicants filing of the parent application, the prior art disclosed the use of the topical application of a wide variety of antibiotics to treat acne using a water/water-miscible alcohol based carrier that enhances penetration of the antibiotic into the canal of the sebaceous follicle.

Heymes (U.S. Pat. No. 4,097,595 patented in 1978) discloses novel 7-amino-thiazolyl-acetamido-cephalosporanic acid compounds of the formula (see patent for chemical structure) wherein R is selected from the group consisting of hydrogen and a group easily removable by acid hydrolysis or hydrogenolysis, R(1)is selected from the group consisting of alkyl of 1 to 4 carbon atoms, a 5 member heterocyclic ring and a 5 member heterocyclic ring containing a ketone group and A is selected from the group consisting of hydrogen, alkali metal and equivalents of alkaline earth metals, magnesium and organic amine having antibiotic activity against gram negative and gram positive bacteria and their preparation and novel intermediates thereof. These cephalosporin derivatives can be applied topically to skin for a number of conditions disclosed at column 4, lines 27-55. There is no disclosure of the treatment of acne or other acneiform disorders. The in vivo examples are only for mice infected by intraperitoneal injection of material containing microorganisms and subcutaneous administration of the cephalosporin.

In Stoughton et al, "Topical Antibiotic Therapy of Acne", Cutis, 1980, February, 25(2):216-218,220, there is a disclosure that a number of vehicles can be used to improve the skin penetrating power of topically applied antibiotics in the treatment of acne. The antibiotics were applied with their respective vehicles whose penetration was being studied, to hairless mouse skin in vitro. The antibiotics that are disclosed as being topically applied to the hairless mouse skin in vitro are erythromycin, cephalexin (a cephalosporin), troleandomycin, and minocycline. It is noted that on page 220, lines 4-6, there is a disclosure that no significant activity was shown by cephalexin in the in vitro skin penetration study.

It is noted in the last footnote on page 218 that Vehicle 3 in the study was "Vehicle/N TM" of Neutrogena Dermatologics. Vehicle 3 includes ethyl alcohol 47.5%, purified water, laureth-4, isopropyl alcohol 4%, and propylene glycol.

In Eady et al, "The Use of Antibiotics in Acne Therapy: Oral or Topical Administration?", J Antimicrob Chemother, 1982, Aug.; 10(2):89-115, there is a disclosure that tetracycline, erythromycin, chloramphenicol, co-trimoxazole, and clindamycin are used topically in the treatment of acne. On page 104, in the second paragraph under "Conclusions", there is a background statement that "Penicillins and cephalosporins currently account for 50-65% of total antibiotic usage . . . ". However, there is no teaching that either penicillins or cephalosporins are used in the treatment of acne.

In Witkowski J. A. and Parish, L. C., "Bacterial skin infections: management of common streptococcal and staphylococcal lesions", Postgrad Med, October 1982, 72 (4), pages 166-8, 171-3, 176-8, and 181-5 in the English language, there is a disclosure that penicillin G, penicillin V, ampicillin, cefaclor (a cephalosporin), cephalexin (a cephalosporin), cefazolin (a cephalosporin), cephradine (a cephalosporin), cloxacillin, dicloxacillin, methicillin, nafcillin, and oxacillin have been used systemically to treat streptococcal and staphylococcal infection (see pages 176-177). Use of topical bacitracin, erythromycin, or neomycin is disclosed on page 182. Systemic use of penicillin is also mentioned on page 182. There is no mention of the use of topical penicillin G, penicillin V, ampicillin, cefaclor (a cephalosporin), cephalexin (a cephalosporin), cefazolin (a cephalosporin), cephradine (a cephalosporin), cloxacillin, dicloxacillin, methicillin, nafcillin, or oxacillin to topically treat streptococcal and staphylococcal infection. Furthermore, there does not appear to be any mention of the treatment of acne, either systemically or topically.

In "Cephalosporin for acne vulgaris" [letter], Sheeler R. D., J Am Acad Dermatol, June 1986, 14 (6), page 1091, there is a disclosure that the cephalosporins, cefodroxil and cefaclor, given orally were effective in reducing lesions of acne vulgaris as a side effect for treating other infections. The oral cephalosporin treatment followed an unsuccessful treatment regimen of using systemic tetracycline and topical benzoyl peroxide. There is no disclosure of the use of the cephalosporins topically to treat acne.

In AHFS Drug Information, 1990, Gerald K. McEvoy, editor, published by American Society of Hospital Pharmacists, entry on "Cephalosporins", pages 82-87, there is a discussion of cephalosporins and treatments employing cephalosporins. However, there is no disclosure of the use of cephalosporins topically. Still further, there is no topical preparation of cephalosporins disclosed. In this respect, there is no disclosure of the use of cephalosporins to treat acne topically.

In U.S. Pat. No. 4,444,755 of Horrobin, issued on Apr. 24, 1984, there is a disclosure that a number of skin disorders can be treated with gamma-linolenic acid or dibromo-gamma-linolenic acid. There is a teaching and claims to the effect that gamma-linolenic acid or dibromo-gamma-linolenic acid serve to increase prostaglandin(1) activity over prostaglandin(2) activity for the treatment a large number of skin conditions which include acne. Use of a beta-lactam antibiotic (e. g. a cephalosporin) is disclosed, and Horrobin (U.S. Pat. No. 4,444,755) teaches that the purpose of using the beta-lactam antibiotic is to enhance utilization of ester reserves of dibromo-gamma-linolenic acid (column 5, lines 63-64). The antibiotic is present in a small amount to enhance the activity of the gamma-linolenic acid which is present in a large amount. The enhancement of prostaglandin(1) series compounds is also the purpose of zinc, and this would be the purpose of "other materials influencing the 1-series/2-series PG balance in the body in favour of 1-series PG's" (column 2, lines 17-19). There is no disclosure of administering a beta-lactam antibiotic (e. g. a cephalosporin) without concomitant administration of a gamma-linolenic acid or dibromo-gamma-linolenic acid. Thus, for approximately seven years before the Applicants invention, the prior art has disclosed the use of a small, optional amount of a cephalosporin to enhance the activity of a large, required amount of administered gamma-linolenic acid or dibromo-gamma-linolenic acid in the treatment of acne.

Research relating to acne has been an active area of investigation for many years. In this respect, many publications in the medical literature have been made since the year 1979 to Feb. 12, 1993 (a date of a comprehensive computer search) relating to acne.

More specifically, a search of the MEDLINE database using Dialog Information Services for articles mentioning "acne" has revealed that in the time period spanning 1979 through Feb. 12, 1993), there were 2,524 articles. Therefore, for this fourteen year period, there was an average of more than 180 articles per year relating to acne treatment.

A more specific breakdown of a specific year versus the number of articles relating to acne treatment for that year is present in the Table as follows:

| Table of Articles | | |
|---|---|---|
| Year | Number of Articles Mentioning Acne | |
| 1979 | 176 | |
| 1980 | 177 | |
| 1981 | 181 | |
| 1982 | 185 | |
| 1983 | 204 | |
| 1984 | 198 | approx. num. before Horrobin: 82 |
| | | approx. num. after Horrobin: 116 |
| 1985 | 206 | |
| 1986 | 189 | |
| 1987 | 182 | |
| 1988 | 200 | |
| 1989 | 160 | |

-continued

Table of Articles

| Year | Number of Articles Mentioning Acne | |
|---|---|---|
| 1990 | 183 | |
| 1991 | 155 | approx. num. before Invention: 39 |
| | | approx. num. after Invention: 116 |
| 1992 | 128 | |
| 1993 | 0 (as of February 12, 1993) | |

It is recalled that Horrobin (U.S. Pat. No. 4,444,755) was published on Apr. 24, 1984, and the Applicants parent patent application was filed Mar. 5, 1991.

From the Table of Articles, the following additional facts are deduced. From the publication of Horrobin on Apr. 24, 1984 (the prior art that discloses the topical treatment of acne using a cephalosporin and gamma-linolenic acid or dibromo-gamma-linolenic acid) to the filing of the Applicants parent application on Mar. 5, 1991, approximately 1,275 articles relating to acne were published in approximately seven years.

Therefore, for approximately seven years before the Applicants filed their parent patent application, the prior art (Horrobin (U.S. Pat. No. 4,444,755)) disclosed the use of a primary active ingredient (gamma-linolenic acid or dibromo-gamma-linolenic acid) optionally with or without a cephalosporin for the topical treatment of acne. Yet, in spite of the other prior art, such as the Frank reference where an antibiotic (other than a cephalosporin) is the sole active ingredient for topical treatment of acne using a water/water-miscible alcohol carrier, only the Applicants provide a method of treating acne topically with simply a composition consisting essentially of a cephalosporin in a carrier which includes water and a water-miscible alcohol.

Moreover, the Horrobin patent does not mention use of conventional topical anti-acne ingredients selected from the group consisting of benzoyl peroxide, sulfur, resorcinol, salicylic acid, and tretinoin for topical treatment of acne. In this respect, only the Applicants invention provides for the topical use of a cephalosporin along with conventional anti-acne ingredients selected from the group consisting of benzoyl peroxide, sulfur, resorcinol, salicylic acid, and tretinoin.

SUMMARY OF THE INVENTION

Accordingly, it is an object of the invention to provide a new topical treatment for acne and acneiform dermal disorders.

Another object of the invention is to provide a new topical treatment for acne which effectively adds to the armamentarium of physicians, and in particular dermatologists, to treat heretofore resistant forms of acne for which there was no safe, minimal side effect, and effective treatment available.

Another object of the invention is to provide a new topical treatment for acne which will avoid the undesirable side effects of the currently available oral antibiotics for the systemic treatment of acne and acneiform dermal disorders, such as diarrhea, abdominal cramping, nausea, vomiting, drug eruptions, photosensitivity, blood dyscrasias (e. g. depression of white blood cell count and red blood cell count), drug induced hepatitis (elevation of liver functions), and teratogenicity, to name a few.

Still another object of the invention is to provide a topical treatment for acne which uses an antibiotic that does not have the risk of bearing a toxic residue of a toxic bridging agent.

In accordance with the invention, a cephalosporin or cephalosporin derivative is mixed with a carrier and applied topically to the skin of a patient suffering from acne which includes acne vulgaris and other acneiform dermal disorders. Suitable cephalosporins include cefaclor, cefadroxil, cefamandole nafate, cefazolin, cefixime, cefmetazole, cefonicid, cefoperazone, cefoxitin, cefpodoxime proxetil, ceftazidime, ceftizoxime, ceftriaxone, ceftriaxone moxalactam (a 1-oxa-beta-lactam), cefuroxime, cephalexin, cephalosporin C cephalosporin C, sodium salt, cephalothin, cephalothin sodium salt, cephapirin, cephradine, the 1-acetyloxy ethyl ester of cefuroxime (cefuroxime-axetil), dihydratecephalothin, and moxalactam.

Cephalosporins are deemed in this patent to include cephalosporin derivatives such as carbacephems, and, more specifically, loracarbef which is marketed by Eli Lilly Co., Indianapolis, Ind., as lorabid. See The Medical Letter, Vol. 34, (Issue 879), pages 87–88, Sep. 18, 1992. More specifically, loracarbef is chemically identical to cefaclor except that the sulfur atom in the dihydrothiazone ring has been replaced by a methylene group to form a tetrahydropyridine ring. See Cooper, Am. J. Med., Vol. 92, Suppl 6A:2S, Jun. 22, 1992. It is thought generally that carbacephems have greater chemical stability in solution. See Pasini et al, Pharm. Res., 9:250, 1992.

It is disclosed in the medical literature that some of the cephalosporins have activity in vitro against Propionibacterium acnes. However, there is no disclosure of using a cephalosporin to topically treat acne. More specifically, the medical literature indicates that the following cephalosporins are active against Propionibacterium acnes in vitro: cefaclor, cefonicid, cefoperazone, cefotanme, cefotetan, ceftazidime, ceftizoxime, ceftriaxone, cefuroxime, and loracarbef.

It is also contemplated that aztreonam can be used topically for treating acne. Aztreonam is marketed by E. R. Squibb and Sons, Inc., Princeton, N.J., under the name Azactam TM. Aztreonam is the first of a new class of antibiotics classified as monobactams.

With the invention, a variety of treatment regimens are contemplated.

In a first treatment regimen, topical compositions of the invention are used alone to treat the acne and acneiform dermal disorders. In this respect, the topical compositions of the invention can be used as a first line treatment for acne and acneiform dermal disorders.

In a second treatment regimen of the invention, an orally administered antibiotic and a topical composition of the invention are used in combination. There are a number of specific courses of treatment that can be carried out in this second treatment regimen. The oral antibiotic and the topical composition of the invention can be administered simultaneously from the beginning. Or, the oral administration can be begun first, and the topical administration can then be begun. The oral administration can continue when the topical administration begins, or the oral administration can stop when the topical administration begins. Alternatively, the oral antibiotic and the topical composition of the invention can be administered sequentially. With sequential administration, oral administration can take place first, and then topical administration can be begun.

In this respect, after a conventional regimen of treating a patient for acne or acneiform dermal disorders with an orally administered antibiotic, such as tetracycline, minocycline, oxycycline, erythromycin, wherein the patient develops resistance or no improvement, it is the teaching of this invention that a cephalosporin is administered topically to the patient.

In a third treatment regimen of the invention, conventional topical medications and topical compositions of the invention can be administered simultaneously. The conventional topical medications which can be used include: benzoyl peroxide and/or topical Retin-A TM (tretinoin) and/or any other topical agent currently used by physicians in the treatment of acne and acneiform dermal disorders.

In a fourth treatment regimen of the invention, conventional oral medications, conventional topical medications, and topical compositions of the invention can be administered simultaneously.

The cephalosporin, or derivative or analog thereof can be administered alone or in conjunction with a nitroimidazole, such as metronidazole, disclosed in U.S. Pat. No. 4,957,918, incorporated herein by reference. Furthermore, the cephalosporin, or derivative or analog thereof can be applied subsequent to treatment with the nitroimidazole compound.

Although the inventors are not bound by any theoretical explanation as to why the compositions and the methods of the invention are efficacious in treating acne and acneiform dermal disorders, presentation of certain theoretical concepts may be of value.

For one thing, it is felt that the efficacy of the compositions and the methods of the invention is due in part to the antibiotic qualities of the compositions employed and the fact that a portion of the topically applied antibiotic is absorbed by the skin and enters the patient's bloodstream.

Another possible reason for the efficacy of the compositions and the methods of the invention is that the compositions of the invention exert an anti-inflammatory effect on the cells of the sebaceous gland unit, thereby decreasing production of neutrophils and lymphocytes which contribute to inflammation.

Still another possible reason for the efficacy of the topical compositions and methods of the invention is that the topically applied antibiotic is able to kill microorganisms that cannot be killed by an orally administered antibiotic. More specifically, the topically applied antibiotic directly kills microorganisms in the sebaceous follicle that are shielded by a hydrophobic sebaceous film inside the follicle from the effects of an antibiotic in the bloodstream. The bloodstream is essentially an aqueous medium, and the hydrophobic sebaceous film blocks the antibiotic in the bloodstream, from diffusing onto the microorganisms on the other side of the sebaceous film. However, the microorganism may produce products that are fat soluble and are able to cross through the sebaceous film and thereby irritate the cells lining the sebaceous follicle. Thus, the hydrophobic sebaceous film may allow passage, in one direction, of irritants from the microorganisms to the follicle walls, but the hydrophobic sebaceous film prevents passage of antibiotic in the bloodstream from diffusing across the hydrophobic sebaceous film in the other direction to the microorganisms.

Even another possible mechanism of action for the efficacy of the compositions and methods of the invention is that the compositions of the invention decrease neutrophil and lymphocyte chemotaxis (this refers to the attraction of blood cells or biologic products toward a region of activity), thereby reducing the inflammatory infiltrate and decreasing the lesion of acne.

DETAILED DESCRIPTION OF PREFERRED EMBODIMENTS

It is understood herein that the term cephalosporin derivative is a compound that contains the following chemical structural components: 3-[(acetyloxy)methyl]-7-[(R-)amino]-8-oxo-5-thia-1-azabicyclo[4.2.0]oct-2-ene-2-carboxylic acid, where R is a reactive group substituted on the nitrogen of the 7-amino group.

It is noted that for cephalosporin C there is a 5-amino-5-carboxy-1-oxopentyl group on the nitrogen of the 7-amino group. More specifically, for cephalosporin C, the "R" in the formula for cephalosporin derivatives is a 5-amino-5-carboxy-1-oxopentyl group.

It is noted that for cephalothin there is a 2-thienyl-5-amino-5-carboxy-1-oxopentyl group on the nitrogen of the 7-amino group. More specifically, for cephalothin, the "R" in the formula for cephalosporin derivatives is a 5-amino-5-carboxy-1-oxopentyl group.

Specific suitable cephalosporin derivatives are as follows: cephalosporin C; cephalosporin C, sodium salt, dihydrate; cephalothin; cephalothin, sodium salt (also known as Averon-1, Cefalotin, Cephation, Ceporacin, Cepovenin, Chephalotin, Coaxin, Keflin, Lospoven, Microtin, Synclotin, and Toricelocin); cephapirin sodium; cefadroxil; cefazolin; cephalexin; cephalothin; cephapirin; cephradine; cefaclor; cefamandole; cefonicid; ceforanide; cefotetan (a cephamycin); cefoxitin (a cephamycin); cefuroxime; the 1-acetyloxy ethyl ester of cefuroxime (cefuroxime axetil and Ceftin); cefoperazone; cefotaxime; cefpodoxime proxetil, ceftazidime; ceftizoxime; ceftriaxone; moxalactam (a 1-oxa-beta-lactam); and loracarbef (lorabid), among others.

In addition, analogs of cephalosporin are also suitable for topical treatment of acne. These cephalosporin analogs include: cephalosporin $P_1$; cephamycins; cepharanthine; and cephradine.

Suitable carriers for the form of cephalosporin or cephalosporin derivative or cephalosporin analog can be selected from the group of pharmaceutical carriers consisting of: a mixture of water and a water-miscible organic solvent, e. g. a water-miscible alcohol; a petrolatum vehicle; a water soluble gel; a mineral oil base; a blend of mineral oil and petrolatum; a suspension of an ion-exchange resin, e. g. Amberlite, in water; and other suitable pharmaceutical carriers, well known in the art.

By selection of a suitable vehicle, the cephalosporin can be administered topically as a solution, a gel, a lotion, a cream, or an ointment. The cephalosporin can also be administered topically using liposomes. The cephalosporin can also be administered topically using a liquid-absorbed wipe material made from fibrous or open-cell foam absorbant material. The cephalosporin can also be administered topically using a slow, time-release patch.

In addition to the form of cephalosporin or cephalosporin derivative or cephalosporin analog that is employed as an active ingredient, another active ingredient, such as benzoyl peroxide can be used.

For a topical formulation, in addition to the form of cephalosporin or cephalosporin derivative or cephalosporin analog, the carrier, and possibly another active ingredient, the formulation can also include an agent which enhances penetration of an active ingredient through the skin. Exemplary agents which increase skin penetration are disclosed in the following U.S. patents all of which are incorporated herein by reference: U.S. Pat. No. 4,537,776 (a binary combination of N-(hydroxyethyl)pyrrolidone and a cell-envelope disordering compound); U.S. Pat. No. 4,130,667 (using a sugar ester in combination with a sulfoxide or phosphine oxide); and U.S. Pat. No. 3,952,099 (using sucrose monooleate, decyl methyl sulfoxide, and alcohol).

Other exemplary materials that increase skin penetration are surfactants or wetting agents which include the following: polyoxyethylene sorbitan mono-oleoate (Polysorbate 80); sorbitan mono-oleate (Span 80); p-isooctyl polyoxyethylene-phenol polymer (Triton WR-1330); polyoxyethylene sorbitan tri-oleate (Tween 85); dioctyl sodium sulphosuccinate; and sodium sarcosinate (Sarcosyl NL-97); and other pharmaceutically acceptable surfactants.

Although there is not a complete understanding of the detailed theoretical mechanism upon which the efficacy of the topical dermatological compositions of the present invention which contain cephalosporins and derivatives are founded, this lack of theoretical understanding in no way diminishes the benefits derived from employing the compositions and methods of the invention and in no way detracts from the utility of the invention as described herein.

Nevertheless, although not proven conclusively, it is felt that the topical use of cephalosporin or cephalosporin derivative or cephalosporin analog of the invention helps diminish the presence of Propionibacterium acnes, and therefore diminish the effects on acne caused by the presence of Propionibacterium acnes.

Furthermore, although not proven conclusively, it is felt that the topical use of cephalosporin or cephalosporin derivative or cephalosporin analog of the invention serves to inhibit the skin's inflammatory response. More specifically, it is felt that by using the principles of the invention, there is a decrease in chemotaxis of lymphocytes and neutrophils toward the pilosebaceous unit where inflammation and follicular plugging, and sebaceous fluid are accumulating. It may be that the major effect of topical cephalosporins is this anti-chemotactic effect of neutrophils and lymphocytes.

A variety of suitable cephalosporin compositions of the invention for topical application to the skin for treating acne and acneiform dermal disorders are presented below in Examples 1-156.

EXAMPLE 1

A topical dermatological composition containing cefaclor is obtained as follows. Mix the following ingredients in the amounts specified.

| Ingredient | Weight Per Cent |
| --- | --- |
| Ethyl alcohol | 41.5 |
| Laureth-4 | 0.5 |
| Isopropyl alcohol | 6.0 |
| cefaclor | 2.0 |
| Purified water | balance |

Citric acid can be used to adjust the pH to a desired level.

The composition in this example contains approximately 2% cefaclor. Other suitable compositions can be made in accordance with this example which include cefaclor in the following percentages: 0.5%, 1%, 3%, 4%, 5%, and 10%.

EXAMPLE 2

A topical dermatological composition containing cefaclor is obtained as follows. Mix the following ingredients in the amounts specified.

| Ingredient | Weight Per Cent |
| --- | --- |
| Ethyl alcohol | 71.2 |
| Propylene glycol | 26.8 |
| cefaclor | 2.0 |

The composition in this example contains approximately 2% cefaclor.

Other topical dermatological compositions are presented below.

EXAMPLE 3

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefaclor (as 0.75% by weight) is prepared as follows. 180 grams of Carbopol 940 ™ (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefaclor dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefaclor in the following percentages: 0.5%, 1%, 2%, 3%, 4%, 5%, and 10%.

EXAMPLE 4

Another topical dermatological gel is obtained by mixing the following ingredients in suitable amounts: allantoin, carbomer 934P, methylparaben, polyethylene glycol 400, propylene glycol, sodium hydroxide, purified water and cefaclor.

EXAMPLE 5

A powdery composition is obtained as follows. Mix the following ingredients in the amounts specified.

| Ingredient | Weight Per Cent |
| --- | --- |
| Benzoyl peroxide (micronized) | 1 to 35 |
| Calcium phosphate | 63 to 98.5 |

| Ingredient | Weight Per Cent |
| --- | --- |
| cefaclor | 0.5 to 5 |

EXAMPLE 6

A liquid composition is obtained as follows. Mix the following ingredients in the amounts specified.

| Ingredient | Weight Per Cent |
| --- | --- |
| cefaclor | 0.5 to 5 |
| Benzoyl peroxide (micronized) | 1 to 30 |
| Ethanol | The Balance to 100% |

EXAMPLE 7

A topical dermatological composition containing cefaclor is obtained as follows. Mix the following ingredients in the amounts specified.

| Ingredient | Weight Per Cent |
| --- | --- |
| Ethyl alcohol | 48.0 |
| Laureth-4 | 0.5 |
| Isopropyl alcohol | 4.0 |
| Propylene glycol | 10.0 |
| cefaclor | 1.0 |
| Purified water | balance |

Citric acid can be used to adjust the pH to a desired level.

The composition in this example contains approximately 1% cefaclor. Other suitable compositions can be made in accordance with this example which include cefaclor in the following percentages: 0.5%, 2%, 3%, 4%, 5%, and 10%.

For Example 8, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 8, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Per Cent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |

| Ingredient in gel carrier | Weight Per Cent in the Final Mixture containing antibiotic, benzoyl peroxide, and gel carrier |
| --- | --- |
| Dioctyl sodium sulfosuccinate | 1.00 |

EXAMPLE 8

A topical dermatological gel composition containing cefaclor antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefaclor (approximately 3 grams of cefaclor). The contents of the first container and the contents of the second container are stable for long periods of time. When the topical composition containing cefaclor and benzoyl peroxide of the invention is to be made, a quantity of 70% ethyl alcohol (e. g. 3 ml.) is added to the second container to dissolve the cefaclor and form an alcoholic solution thereof. Then the alcoholic solution of cefaclor is added to the first container, and all the ingredients are mixed to form the topical gel composition of the invention which contains both cefaclor and benzoyl peroxide. This composition of the invention is stable, under refrigeration, for approximately 3 months.

More specifically, the blended topical gel composition of the invention with contains cefaclor and benzoyl peroxide in a gel carrier or vehicle has the following components in the approximate amounts specified.

| Ingredient | Weight Per Cent |
| --- | --- |
| cefaclor | 3.0 |
| Benzoyl peroxide | 5.0 |
| Gel carrier or vehicle | 92.0 |

Citric acid can be used to adjust the pH to a desired level.

The composition in this example contains approximately 3% cefaclor. Other suitable compositions can be made in accordance with this example which include cefaclor in the following percentages: 0.5%, 1%, 2%, 4%, 5%, and 10%.

EXAMPLE 9

A dermatological lotion containing cefaclor is obtained by mixing the following ingredients in the amounts specified. The ingredients in Container A is blended with the ingredients in Container B.

| Ingredient | Weight Per Cent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |

| Ingredient | Weight Per Cent of ingredient in overall lotion |
|---|---|
| In Container B: | |
| Acetone | 3.00 |
| cefaclor | 3.00 |

Citric acid can be used to adjust the pH to a desired level.

To obtain the lotion composition in this example, the composition in Container A is prepared. This composition in Container A is stable for long periods of time.

Container B can contain only cefaclor for a long period of time. Just prior to forming the complete lotion composition, 3 grams of acetone are added to Container B to dissolve the cefaclor. Then, the contents of Container A and Container B are combined to form the complete lotion composition of the invention.

The composition in this example contains approximately 3% cefaclor. Other suitable compositions can be made in accordance with Example 62 which include cefaclor in the following percentages: 0.5%, 1%, 2%, 4%, 5%, and 10%.

EXAMPLE 10

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefaclor | 2 |

Other suitable compositions can be made in accordance with this example which include cefaclor in the following percentages: 0.5%, 1%, 3%, 4%, 5%, and 10%.

EXAMPLE 11

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefaclor | 3 |

Other suitable compositions can be made in accordance with this example which include cefaclor in the following percentages: 0.5%, 1%, 2%, 4%, 5%, and 10%.

EXAMPLE 12

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefaclor | 3 |

Other suitable compositions can be made in accordance with this example which include cefaclor in the following percentages: 0.5%, 1%, 2%, 4%, 5%, and 10%.

EXAMPLE 13

A gel composition is obtained as follows. Mix the following ingredients in the amounts specified.

| Ingredient | Weight Per Cent |
|---|---|
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolazine | 0.75 |
| cefaclor | 3 |

Other suitable compositions can be made in accordance with this example which include cefaclor in the following percentages: 0.5%, 1%, 2%, 4%, 5%, and 10%.

EXAMPLE 14

A suspension composition is obtained as follows. Mix the following ingredients in the amounts specified.

| Ingredient | Weight Per Cent |
|---|---|
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cefaclor | 2 |

Other suitable compositions can be made in accordance with this example which include cefaclor in the following percentages: 0.5%, 1%, 3%, 4%, 5%, and 10%.

EXAMPLE 15

A dermatological lotion is obtained by mixing the following ingredients in suitable amounts: amoxicillin (approximately 1% by weight); and a carrier which includes isopropyl alcohol (approximately 80% by weight), purified water (approximately 9% by weight), and propylene glycol (approximately 10% by weight).

EXAMPLE 16

An oil-in-water emulsion containing cefaclor in ointment form is obtained as follows.

Part A is comprised of a 3.33% aqueous solution of cefaclor.

Part B is an ointment base comprised of:

| Ingredient | Weight Per Cent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefaclor. Other suitable compositions can be made in accordance with this example which include cefaclor in the following percentages: 0.5%, 1%, 3%, 4%, 5%, and 10%.

EXAMPLE 17

A mineral-oil-based cefaclor ointment is obtained as follows.

Part A is comprised of a 6.66% aqueous solution of cefaclor.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefaclor. Other suitable compositions can be made in accordance with this example which include cefaclor in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 18

A topical dermatological composition containing cefuroxime is obtained as follows. Mix the following ingredients in the amounts specified.

| Ingredient | Weight Per Cent |
|---|---|
| Ethyl alcohol | 41.5 |
| Laureth-4 | 0.5 |
| Isopropyl alcohol | 6.0 |
| cefuroxime | 2.0 |
| Purified water | balance |

Citric acid can be used to adjust the pH to a desired level.

The composition in this example contains approximately 2% cefuroxime. Other suitable compositions can be made in accordance with this example which include cefuroxime in the following percentages: 0.5%, 1%, 3%, 4%, 5%, and 10%.

EXAMPLE 19

A topical dermatological composition containing cefuroxime is obtained as follows. Mix the following ingredients in the amounts specified.

| Ingredient | Weight Per Cent |
|---|---|
| Ethyl alcohol | 71.2 |
| Propylene glycol | 26.8 |
| cefuroxime | 2.0 |

The composition in this example contains approximately 2% cefuroxime.

Other topical dermatological compositions are presented below.

EXAMPLE 20

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefuroxime (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefuroxime dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefuroxime in the following percentages: 0.5%, 1%, 2%, 3%, 4%, 5%, and 10%.

EXAMPLE 21

Another topical dermatological gel is obtained by mixing the following ingredients in suitable amounts: allantoin, carbomer 934P, methylparaben, polyethylene glycol 400, propylene glycol, sodium hydroxide, purified water and cefuroxime.

EXAMPLE 22

A powdery composition is obtained as follows. Mix the following ingredients in the amounts specified.

| Ingredient | Weight Per Cent |
| --- | --- |
| Benzoyl peroxide (micronized) | 1 to 35 |
| Calcium phosphate | 63 to 98.5 |
| cefuroxime | 0.5 to 5 |

EXAMPLE 23

A liquid composition is obtained as follows. Mix the following ingredients in the amounts specified.

| Ingredient | Weight Per Cent |
| --- | --- |
| cefuroxime | 0.5 to 5 |
| Benzoyl peroxide (micronized) | 1 to 30 |
| Ethanol | The Balance to 100% |

EXAMPLE 24

A topical dermatological composition containing cefuroxime is obtained as follows. Mix the following ingredients in the amounts specified.

| Ingredient | Weight Per Cent |
| --- | --- |
| Ethyl alcohol | 48.0 |
| Laureth-4 | 0.5 |
| Isopropyl alcohol | 4.0 |
| Propylene glycol | 10.0 |
| cefuroxime | 1.0 |
| Purified water | balance |

Citric acid can be used to adjust the pH to a desired level.

The composition in this example contains approximately 1% cefuroxime. Other suitable compositions can be made in accordance with this example which include cefuroxime in the following percentages: 0.5%, 2%, 3%, 4%, 5%, and 10%.

For Example 25, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 25, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Per Cent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 25

A topical dermatological gel composition containing cefuroxime antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefuroxime (approximately 3 grams of cefuroxime). The contents of the first container and the contents of the second container are stable for long periods of time. When the topical composition containing cefuroxime and benzoyl peroxide of the invention is to be made, a quantity of 70% ethyl alcohol (e. g. 3 ml.) is added to the second container to dissolve the cefuroxime and form an alcoholic solution thereof. Then the alcoholic solution of cefuroxime is added to the first container, and all the ingredients are mixed to form the topical gel composition of the invention which contains both cefuroxime and benzoyl peroxide. This composition of the invention is stable, under refrigeration, for approximately 3 months.

More specifically, the blended topical gel composition of the invention with contains cefuroxime and benzoyl peroxide in a gel carrier or vehicle has the following components in the approximate amounts specified.

| Ingredient | Weight Per Cent |
| --- | --- |
| cefuroxime | 3.0 |
| Benzoyl peroxide | 5.0 |
| Gel carrier or vehicle | 92.0 |

Citric acid can be used to adjust the pH to a desired level.

The composition in this example contains approximately 3% cefuroxime. Other suitable compositions can be made in accordance with this example which include cefuroxime in the following percentages: 0.5%, 1%, 2%, 4%, 5%, and 10%.

EXAMPLE 26

A dermatological lotion containing cefuroxime is obtained by mixing the following ingredients in the amounts specified. The ingredients in Container A is blended with the ingredients in Container B.

| Ingredient | Weight Per Cent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cefuroxime | 3.00 |

Citric acid can be used to adjust the pH to a desired level.

To obtain the lotion composition in this example, the composition in Container A is prepared. This composition in Container A is stable for long periods of time.

Container B can contain only cefuroxime for a long period of time. Just prior to forming the complete lotion composition, 3 grams of acetone are added to Container B to dissolve the cefuroxime. Then, the contents of Container A and Container B are combined to form the complete lotion composition of the invention.

The composition in this example contains approximately 3% cefuroxime. Other suitable compositions can be made in accordance with Example 62 which include cefuroxime in the following percentages: 0.5%, 1%, 2%, 4%, 5%, and 10%.

EXAMPLE 27

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefuroxime | 2 |

Other suitable compositions can be made in accordance with this example which include cefuroxime in the following percentages: 0.5%, 1%, 3%, 4%, 5%, and 10%.

EXAMPLE 28

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefuroxime | 3 |

Other suitable compositions can be made in accordance with this example which include cefuroxime in the following percentages: 0.5%, 1%, 2%, 4%, 5%, and 10%.

EXAMPLE 29

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefuroxime | 3 |

Other suitable compositions can be made in accordance with this example which include cefuroxime in the following percentages: 0.5%, 1%, 2%, 4%, 5%, and 10%.

EXAMPLE 30

A gel composition is obtained as follows. Mix the following ingredients in the amounts specified.

| Ingredient | Weight Per Cent |
|---|---|
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cefuroxime | 3 |

Other suitable compositions can be made in accordance with this example which include cefuroxime in the following percentages: 0.5%, 1%, 2%, 4%, 5%, and 10%.

EXAMPLE 31

A suspension composition is obtained as follows. Mix the following ingredients in the amounts specified.

| Ingredient | Weight Per Cent |
|---|---|
| Water, deionized or distilled | 54.97 |
| Butylated hydroxyanisole | 0.10 |
| Benzoyl peroxide (micronized) | 5 |
| Dioctyl sodium sulphosuccinate | 1 |

-continued

| Ingredient | Weight Per Cent |
|---|---|
| Colloidal Bentonite | 1.5 |
| Carboxy vinyl polymer (acid form) | 0.25 |
| Ethyl alcohol | 35 |
| Diisopropanolamine | 0.18 |
| cefuroxime | 2 |

Other suitable compositions can be made in accordance with this example which include cefuroxime in the following percentages: 0.5%, 1%, 3%, 4%, 5%, and 10%.

EXAMPLE 32

A dermatological lotion is obtained by mixing the following ingredients in suitable amounts: amoxicillin (approximately 1% by weight); and a carrier which includes isopropyl alcohol (approximately 80% by weight), purified water (approximately 9% by weight), and propylene glycol (approximately 10% by weight).

EXAMPLE 33

An oil-in-water emulsion containing cefuroxime in ointment form is obtained as follows.

Part A is comprised of a 3.33% aqueous solution of cefuroxime.

Part B is an ointment base comprised of:

| Ingredient | Weight Per Cent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefuroxime. Other suitable compositions can be made in accordance with this example which include cefuroxime in the following percentages: 0.5%, 1%, 3%, 4%, 5%, and 10%.

EXAMPLE 34

A mineral-oil-based cefuroxime ointment is obtained as follows.

Part A is comprised of a 6.66% aqueous solution of cefuroxime.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefuroxime. Other suitable compositions can be made in accordance with this example which include cefuroxime in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 35

A topical dermatological composition containing cefuroxime-axetil is obtained as follows. Mix the following ingredients in the amounts specified.

| Ingredient | Weight Per Cent |
|---|---|
| Ethyl alcohol | 41.5 |
| Laureth-4 | 0.5 |
| Isopropyl alcohol | 6.0 |
| cefuroxime-axetil | 2.0 |
| Purified water | balance |

Citric acid can be used to adjust the pH to a desired level.

The composition in this example contains approximately 2% cefuroxime-axetil. Other suitable compositions can be made in accordance with this example which include cefuroxime-axetil in the following percentages: 0.5%, 1%, 3%, 4%, 5%, and 10%.

EXAMPLE 36

A topical dermatological composition containing cefuroxime-axetil is obtained as follows. Mix the following ingredients in the amounts specified.

| Ingredient | Weight Per Cent |
|---|---|
| Ethyl alcohol | 71.2 |
| Propylene glycol | 26.8 |
| cefuroxime-axetil | 2.0 |

The composition in this example contains approximately 2% cefuroxime-axetil.

Other topical dermatological compositions are presented below.

EXAMPLE 37

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefuroxime-axetil (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefuroxime-axetil dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefuroxime-axetil in the following percentages: 0.5%, 1%, 2%, 3%, 4%, 5%, and 10%.

EXAMPLE 38

Another topical dermatological gel is obtained by mixing the following ingredients in suitable amounts: allantoin, carbomer 934P, methylparaben, polyethylene glycol 400, propylene glycol, sodium hydroxide, purified water and cefuroxime-axetil.

EXAMPLE 39

A powdery composition is obtained as follows. Mix the following ingredients in the amounts specified.

| Ingredient | Weight Per Cent |
|---|---|
| Benzoyl peroxide (micronized) | 1 to 35 |
| Calcium phosphate | 63 to 98.5 |
| cefuroxime-axetil | 0.5 to 5 |

EXAMPLE 40

A liquid composition is obtained as follows. Mix the following ingredients in the amounts specified.

| Ingredient | Weight Per Cent |
|---|---|
| cefuroxime-axetil | 0.5 to 5 |
| Benzoyl peroxide (micronized) | 1 to 30 |
| Ethanol | The Balance to 100% |

EXAMPLE 41

A topical dermatological composition containing cefuroxime-axetil is obtained as follows. Mix the following ingredients in the amounts specified.

| Ingredient | Weight Per Cent |
|---|---|
| Ethyl alcohol | 48.0 |
| Laureth-4 | 0.5 |
| Isopropyl alcohol | 4.0 |
| Propylene glycol | 10.0 |
| cefuroxime-axetil | 1.0 |
| Purified water | balance |

Citric acid can be used to adjust the pH to a desired level.

The composition in this example contains approximately 1% cefuroxime-axetil. Other suitable compositions can be made in accordance with this example which include cefuroxime-axetil in the following percentages: 0.5%, 2%, 3%, 4%, 5%, and 10%.

For Example 42, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 42, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Per Cent in the Final Mixture containing antibiotic, benzoyl peroxide, and gel carrier |
|---|---|
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 42

A topical dermatological gel composition containing cefuroxime-axetil antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefuroxime-axetil (approximately 3 grams of cefuroxime-axetil). The contents of the first container and the contents of the second container are stable for long periods of time. When the topical composition containing cefuroxime-axetil and benzoyl peroxide of the invention is to be made, a quantity of 70% ethyl alcohol (e. g. 3 ml.) is added to the second container to dissolve the cefuroxime-axetil and form an alcoholic solution thereof. Then the alcoholic solution of cefuroxime-axetil is added to the first container, and all the ingredients are mixed to form the topical gel composition of the invention which contains both cefuroxime-axetil and benzoyl peroxide. This composition of the invention is stable, under refrigeration, for approximately 3 months.

More specifically, the blended topical gel composition of the invention with contains cefuroxime-axetil and benzoyl peroxide in a gel carrier or vehicle has the following components in the approximate amounts specified.

| Ingredient | Weight Per Cent |
|---|---|
| cefuroxime-axetil | 3.0 |
| Benzoyl peroxide | 5.0 |
| Gel carrier or vehicle | 92.0 |

Citric acid can be used to adjust the pH to a desired level.

The composition in this example contains approximately 3% cefuroxime-axetil. Other suitable compositions can be made in accordance with this example which include cefuroxime-axetil in the following percentages: 0.5%, 1%, 2%, 4%, 5%, and 10%.

EXAMPLE 43

A dermatological lotion containing cefuroxime-axetil is obtained by mixing the following ingredients in the amounts specified. The ingredients in Container A is blended with the ingredients in Container B.

| Ingredient | Weight Per Cent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cefuroxime-axetil | 3.00 |

Citric acid can be used to adjust the pH to a desired level.

To obtain the lotion composition in this example, the composition in Container A is prepared. This composition in Container A is stable for long periods of time.

Container B can contain only cefuroxime-axetil for a long period of time. Just prior to forming the complete lotion composition, 3 grams of acetone are added to Container B to dissolve the cefuroxime-axetil. Then, the contents of Container A and Container B are combined to form the complete lotion composition of the invention.

The composition in this example contains approximately 3% cefuroxime-axetil. Other suitable compositions can be made in accordance with Example 62 which include cefuroxime-axetil in the following percentages: 0.5%, 1%, 2%, 4%, 5%, and 10%.

EXAMPLE 44

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefuroxime-axetil | 2 |

Other suitable compositions can be made in accordance with this example which include cefuroxime-axetil in the following percentages: 0.5%, 1%, 3%, 4%, 5%, and 10%.

EXAMPLE 45

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefuroxime-axetil | 3 |

Other suitable compositions can be made in accordance with this example which include cefuroxime-axetil in the following percentages: 0.5%, 1%, 2%, 4%, 5%, and 10%.

EXAMPLE 46

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefuroxime-axetil | 3 |

Other suitable compositions can be made in accordance with this example which include cefuroxime-axetil in the following percentages: 0.5%, 1%, 2%, 4%, 5%, and 10%.

EXAMPLE 47

A gel composition is obtained as follows. Mix the following ingredients in the amounts specified.

| Ingredient | Weight Percent |
|---|---|
| Water, deionized or distilled | 51.65 |

-continued

| Ingredient | Weight Percent |
| --- | --- |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cefuroxime-axetil | 3 |

Other suitable compositions can be made in accordance with this example which include cefuroxime-axetil in the following percentages: 0.5%, 1%, 2%, 4%, 5%, and 10%.

EXAMPLE 48

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cefuroxime-axetil | 2 |

Other suitable compositions can be made in accordance with this example which include cefuroxime-axetil in the following percentages: 0.5%, 1%, 3%, 4%, 5%, and 10%.

EXAMPLE 49

A dermatological lotion is obtained by mixing the following ingredients in suitable amounts: cefaclor (approximately 1% by weight); and a carrier which includes isopropyl alcohol (approximately 80% by weight), purified water (approximately 9% by weight), and propylene glycol (approximately 10% by weight).

EXAMPLE 50

An oil-in-water emulsion containing cefuroxime-axetil in ointment form is obtained as follows.

Part A is comprised of a 3.33% aqueous solution of cefuroxime-axetil.

Part B is an ointment base comprised of:

| Ingredient | Weight Percent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefuroxime-axetil. Other suitable compositions can be made in accordance with this example which include cefuroxime-axetil in the following percentages: 0.5%, 1%, 3%, 4%, 5%, and 10%.

EXAMPLE 51

A mineral-oil-based cefuroxime-axetil ointment is obtained as follows.

Part A is comprised of a 6.66% aqueous solution of cefuroxime-axetil.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefuroxime-axetil. Other suitable compositions can be made in accordance with this example which include cefuroxime-axetil in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.). Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 52

A topical dermatological composition containing cefotetan is obtained as follows. Mix the following ingredients in the amounts specified.

| Ingredient | Weight Percent |
| --- | --- |
| Ethyl alcohol | 41.5 |
| Laureth-4 | 0.5 |
| Isopropyl alcohol | 6.0 |
| cefotetan | 2.0 |
| Purified water | balance |

Citric acid can be used to adjust the pH to a desired level.

The composition in this example contains approximately 2% cefotetan. Other suitable compositions can be made in accordance with this example which include cefotetan in the following percentages: 0.5%, 1%, 3%, 4%, 5%, and 10%.

EXAMPLE 53

A topical dermatological composition containing cefotetan is obtained as follows. Mix the following ingredients in the amounts specified.

| Ingredient | Weight Percent |
| --- | --- |
| Ethyl alcohol | 71.2 |
| Propylene glycol | 26.8 |
| cefotetan | 2.0 |

The composition in this example contains approximately 2% cefotetan.

Other topical dermatological compositions are presented below.

EXAMPLE 54

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefotetan (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefotetan dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefotetan in the following percentages: 0.5%, 1%, 2%, 3%, 4%, 5%, and 10%.

EXAMPLE 55

Another topical dermatological gel is obtained by mixing the following ingredients in suitable amounts: allantoin, carbomer 934P, methylparaben, polyethylene glycol 400, propylene glycol, sodium hydroxide, purified water and cefotetan.

EXAMPLE 56

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| cefotetan | 0.5 to 5 |

EXAMPLE 57

A liquid composition is obtained as follows. Mix the following ingredients in the amounts specified.

| Ingredient | Weight Percent |
| --- | --- |
| cefotetan | 0.5 to 5 |
| Benzoyl peroxide (micronized) | 1 to 30 |
| Ethanol | The Balance to 100% |

EXAMPLE 58

A topical dermatological composition containing cefotetan is obtained as follows. Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| cefotetan | 1.0 |
| Purified water | balance |

Citric acid can be used to adjust the pH to a desired level.

The composition in this example contains approximately 1% cefotetan. Other suitable compositions can be made in accordance with this example which include cefotetan in the following percentages: 0.5%, 2%, 3%, 4%, 5%, and 10%.

For Example 59, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 59, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Per Cent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |

| Ingredient in gel carrier | Weight Per Cent in the Final Mixture containing antibiotic, benzoyl peroxide, and gel carrier |
|---|---|
| Diisopropanolamine | 0.75 |
| Ethyl alcohol | 32.00 |
| Dioctyl sodium sulfosuccinate | 1.00 |

EXAMPLE 59

A topical dermatological gel composition containing cefotetan antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefotetan (approximately 3 grams of cefotetan). The contents of the first container and the contents of the second container are stable for long periods of time. When the topical composition containing cefotetan and benzoyl peroxide of the invention is to be made, a quantity of 70% ethyl alcohol (e. g. 3 ml.) is added to the second container to dissolve the cefotetan and form an alcoholic solution thereof. Then the alcoholic solution of cefotetan is added to the first container, and all the ingredients are mixed to form the topical gel composition of the invention which contains both cefotetan and benzoyl peroxide. This composition of the invention is stable, under refrigeration, for approximately 3 months.

More specifically, the blended topical gel composition of the invention with contains cefotetan and benzoyl peroxide in a gel carrier or vehicle has the following components in the approximate amounts specified.

| Ingredient | Weight Percent |
|---|---|
| cefotetan | 3.0 |
| Benzoyl peroxide | 5.0 |
| Gel carrier or vehicle | 92.0 |

Citric acid can be used to adjust the pH to a desired level.

The composition in this example contains approximately 3% cefotetan. Other suitable compositions can be made in accordance with this example which include cefotetan in the following percentages: 0.5%, 1%, 2%, 4%, 5%, and 10%.

EXAMPLE 60

A dermatological lotion containing cefotetan is obtained by mixing the following ingredients in the amounts specified. The ingredients in Container A is blended with the ingredients in Container B.

| Ingredient | Weight Percent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cefotetan | 3.00 |

Citric acid can be used to adjust the pH to a desired level.

To obtain the lotion composition in this example, the composition in Container A is prepared. This composition in Container A is stable for long periods of time.

Container B can contain only cefotetan for a long period of time. Just prior to forming the complete lotion composition, 3 grams of acetone are added to Container B to dissolve the cefotetan. Then, the contents of Container A and Container B are combined to form the complete lotion composition of the invention.

The composition in this example contains approximately 3% cefotetan. Other suitable compositions can be made in accordance with Example 62 which include cefotetan in the following percentages: 0.5%, 1%, 2%, 4%, 5%, and 10%.

EXAMPLE 61

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefotetan | 2 |

Other suitable compositions can be made in accordance with this example which include cefotetan in the following percentages: 0.5%, 1%, 3%, 4%, 5%, and 10%.

EXAMPLE 62

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefotetan | 3 |

Other suitable compositions can be made in accordance with this example which include cefotetan in the

EXAMPLE 63

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefotetan | 3 |

Other suitable compositions can be made in accordance with this example which include cefotetan in the following percentages: 0.5%, 1%, 2%, 4%, 5%, and 10%.

EXAMPLE 64

A gel composition is obtained as follows. Mix the following ingredients in the amounts specified.

| Ingredient | Weight Percent |
| --- | --- |
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cefotetan | 3 |

Other suitable compositions can be made in accordance with this example which include cefotetan in the following percentages: 0.5%, 1%, 2%, 4%, 5%, and 10%.

EXAMPLE 65

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cefotetan | 2 |

Other suitable compositions can be made in accordance with this example which include cefotetan in the following percentages: 0.5%, 1%, 3%, 4%, 5%, and 10%.

EXAMPLE 66

A dermatological lotion is obtained by mixing the following ingredients in suitable amounts: cefotetan (approximately 1% by weight); and a carrier which includes isopropyl alcohol (approximately 80% by weight), purified water (approximately 9% by weight), and propylene glycol (approximately 10% by weight).

EXAMPLE 67

An oil-in-water emulsion containing cefotetan in ointment form is obtained as follows.

Part A is comprised of a 3.33% aqueous solution of cefotetan.

Part B is an ointment base comprised of:

| Ingredient | Weight Percent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefotetan. Other suitable compositions can be made in accordance with this example which include cefotetan in the following percentages: 0.5%, 1%, 3%, 4%, 5%, and 10%.

EXAMPLE 68

A mineral-oil-based cefotetan ointment is obtained as follows.

Part A is comprised of a 6.66% aqueous solution of cefotetan.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefotetan. Other suitable compositions can be made in accordance with this example which include cefotetan in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g. × 6.66%) and approximately 28 grams of water (30 g. × 93.34%) are obtained.

By taking 70 ml. of part B, approximately 3.9 grams of isopropyl alcohol (5 ml. × 0.78 g/ml.), approximately 6.25 grams of glycerin (5 ml. × 1.25 g/ml.), and approximately 51 grams of mineral oil (60 ml. × 0.85 g/ml.) are obtained. The weight of 70 ml. of part B is approximately 61.15 grams (3.9 g. + 6.25 g. + 51 g.)

Therefore, the total weight of parts A and B combined is approximately 91.15 grams (30 g. + 61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 69

A topical dermatological composition containing cephalexin is obtained as follows. Mix the following ingredients in the amounts specified.

| Ingredient | Weight Percent |
| --- | --- |
| Ethyl alcohol | 41.5 |
| Laureth-4 | 0.5 |
| Isopropyl alcohol | 6.0 |
| cephalexin | 2.0 |
| Purified water | balance |

Citric acid can be used to adjust the pH to a desired level.

The composition in this example contains approximately 2% cephalexin. Other suitable compositions can be made in accordance with this example which include cephalexin in the following percentages: 0.5%, 1%, 3%, 4%, 5%, and 10%.

EXAMPLE 70

A topical dermatological composition containing cephalexin is obtained as follows. Mix the following ingredients in the amounts specified.

| Ingredient | Weight Percent |
| --- | --- |
| Ethyl alcohol | 71.2 |
| Propylene glycol | 26.8 |
| cephalexin | 2.0 |

The composition in this example contains approximately 2% cephalexin.

Other topical dermatological compositions are presented below.

EXAMPLE 71

A formulation employing a water soluble gel as a carrier is obtained as follows. More details of the gel carrier are described in U.S. Pat. No. 4,837,378, incorporated herein by reference.

A 30 kilogram batch of a composition of the present invention containing cephalexin (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cephalexin dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cephalexin in the following percentages: 0.5%, 1%, 2%, 3%, 4%, 5%, and 10%.

EXAMPLE 72

Another topical dermatological gel is obtained by mixing the following ingredients in suitable amounts: allantoin, carbomer 934P, methylparaben, polyethylene glycol 400, propylene glycol, sodium hydroxide, purified water and cephalexin.

EXAMPLE 73

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| cephalexin | 0.5 to 5 |

EXAMPLE 74

A liquid composition is obtained as follows. Mix the following ingredients in the amounts specified.

| Ingredient | Weight Percent |
| --- | --- |
| cephalexin | 0.5 to 5 |
| Benzoyl peroxide (micronized) | 1 to 30 |
| Ethanol | The Balance to 100% |

EXAMPLE 75

A topical dermatological composition containing cephalexin is obtained as follows. Mix the following ingredients in the amounts specified.

| Ingredient | Weight Percent |
| --- | --- |
| Ethyl alcohol | 48.0 |
| Laureth-4 | 0.5 |
| Isopropyl alcohol | 4.0 |
| Propylene glycol | 10.0 |
| cephalexin | 1.0 |
| Purified water | balance |

Citric acid can be used to adjust the pH to a desired level.

The composition in this example contains approximately 1% cephalexin. Other suitable compositions can be made in accordance with this example which include cephalexin in the following percentages: 0.5%, 2%, 3%, 4%, 5%, and 10%.

For Example 76, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 76, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
|---|---|
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 76

A topical dermatological gel composition containing cephalexin antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cephalexin (approximately 3 grams of cephalexin). The contents of the first container and the contents of the second container are stable for long periods of time. When the topical composition containing cephalexin and benzoyl peroxide of the invention is to be made, a quantity of 70% ethyl alcohol (e. g. 3 ml.) is added to the second container to dissolve the cephalexin and form an alcoholic solution thereof. Then the alcoholic solution of cephalexin is added to the first container, and all the ingredients are mixed to form the topical gel composition of the invention which contains both cephalexin and benzoyl peroxide. This composition of the invention is stable, under refrigeration, for approximately 3 months.

More specifically, the blended topical gel composition of the invention with contains cephalexin and benzoyl peroxide in a gel carrier or vehicle has the following components in the approximate amounts specified.

| Ingredient | Weight Percent |
|---|---|
| cephalexin | 3.0 |
| Benzoyl peroxide | 5.0 |
| Gel carrier or vehicle | 92.0 |

Citric acid can be used to adjust the pH to a desired level.

The composition in this example contains approximately 3% cephalexin. Other suitable compositions can be made in accordance with this example which include cephalexin in the following percentages: 0.5%, 1%, 2%, 4%, 5%, and 10%.

EXAMPLE 77

A dermatological lotion containing cephalexin is obtained by mixing the following ingredients in the amounts specified. The ingredients in Container A is blended with the ingredients in Container B.

| Ingredient | Weight Percent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cephalexin | 3.00 |

Citric acid can be used to adjust the pH to a desired level.

To obtain the lotion composition in this example, the composition in Container A is prepared. This composition in Container A is stable for long periods of time.

Container B can contain only cephalexin for a long period of time. Just prior to forming the complete lotion composition, 3 grams of acetone are added to Container B to dissolve the cephalexin. Then, the contents of Container A and Container B are combined to form the complete lotion composition of the invention.

The composition in this example contains approximately 3% cephalexin. Other suitable compositions can be made in accordance with Example 62 which include cephalexin in the following percentages: 0.5%, 1%, 2%, 4%, 5%, and 10%.

EXAMPLE 78

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cephalexin | 2 |

Other suitable compositions can be made in accordance with this example which include cephalexin in the following percentages: 0.5%, 1%, 3%, 4%, 5%, and 10%.

EXAMPLE 79

A cream composition is obtained as follows. Mix the following ingredients in the amounts specified.

| Ingredient | Weight Percent |
|---|---|
| Ethoxylated cetyl-stearyl alcohol | 15 |

| Ingredient | Weight Percent |
| --- | --- |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalexin | 3 |

Other suitable compositions can be made in accordance with this example which include cephalexin in the following percentages: 0.5%, 1%, 2%, 4%, 5%, and 10%.

EXAMPLE 80

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalexin | 3 |

Other suitable compositions can be made in accordance with this example which include cephalexin in the following percentages: 0.5%, 1%, 2%, 4%, 5%, and 10%.

EXAMPLE 81

A gel composition is obtained as follows. Mix the following ingredients in the amounts specified.

| Ingredient | Weight Percent |
| --- | --- |
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cephalexin | 3 |

Other suitable compositions can be made in accordance with this example which include cephalexin in the following percentages: 0.5%, 1%, 2%, 4%, 5%, and 10%.

EXAMPLE 82

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cephalexin | 2 |

Other suitable compositions can be made in accordance with this example which include cephalexin in the following percentages: 0.5%, 1%, 3%, 4%, 5%, and 10%.

EXAMPLE 83

A dermatological lotion is obtained by mixing the following ingredients in suitable amounts: cephalexin (approximately 1% by weight); and a carrier which includes isopropyl alcohol (approximately 80% by weight), purified water (approximately 9% by weight), and propylene glycol (approximately 10% by weight).

EXAMPLE 84

An oil-in-water emulsion containing cephalexin in ointment form is obtained as follows.

Part A is comprised of a 3.33% aqueous solution of cephalexin.

Part B is an ointment base comprised of:

| Ingredient | Weight Percent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cephalexin. Other suitable compositions can be made in accordance with this example which include cephalexin in the following percentages: 0.5%, 1%, 3%, 4%, 5%, and 10%.

EXAMPLE 85

A mineral-oil-based cephalexin ointment is obtained as follows.

Part A is comprised of a 6.66% aqueous solution of cephalexin.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cephalexin. Other suitable compositions can be made in accordance with this example which include cephalexin in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed.

The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g. $\times$ 6.66%) and approximately 28 grams of water (30 g. $\times$ 93.34%) are obtained.

By taking 70 ml. of part B, approximately 3.9 grams of isopropyl alcohol (5 ml. $\times$ 0.78 g/ml.), approximately 6.25 grams of glycerin (5 ml. $\times$ 1.25 g/ml.), and approximately 51 grams of mineral oil (60 ml. $\times$ 0.85 g/ml.) are obtained. The weight of 70 ml. of part B is approximately 61.15 grams (3.9 g. +6.25 g. +51 g.).

Therefore, the total weight of parts A and B combined is approximately 91.15 grams (30 g. +61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3% +6.86%). It is also noted that the combined weight percentages of the water and water-miscible alcohols is approximately 42.2% (31% +11.2%).

EXAMPLE 86

A topical dermatological composition containing cephalothin is obtained as follows. Mix the following ingredients in the amounts specified.

| Ingredient | Weight Percent |
| --- | --- |
| Ethyl alcohol | 41.5 |
| laureth-4 | 0.5 |
| Isopropyl alcohol | 6.0 |
| cephalothin | 2.0 |
| Purified water | balance |

Citric acid can be used to adjust the pH to a desired level.

The composition in this example contains approximately 2% cephalothin. Other suitable compositions can be made in accordance with this example which include cephalothin in the following percentages: 0.5%, 1%, 3%, 4%, 5%, and 10%.

EXAMPLE 87

A topical dermatological composition containing cephalothin is obtained as follows. Mix the following ingredients in the amounts specified.

| Ingredient | Weight Percent |
| --- | --- |
| Ethyl alcohol | 71.2 |
| Propylene glycol | 26.8 |
| cephalothin | 2.0 |

The composition in this example contains approximately 2% cephalothin.

Other topical dermatological compositions are presented below.

EXAMPLE 88

A formulation employing a water soluble gel as a carrier is obtained as follows. More details of the gel carrier are described in U.S. Pat. No. 4,837,378, incorporated herein by reference.

A 30 kilogram batch of a composition of the present invention containing cephalothin (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cephalothin dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cephalothin in the following percentages: 0.5%, 1%, 2%, 3%, 4%, 5%, and 10%.

EXAMPLE 89

Another topical dermatological gel is obtained by mixing the following ingredients in suitable amounts: allantoin, carbomer 934P, methylparaben, polyethylene glycol 400, propylene glycol, sodium hydroxide, purified water and cephalothin.

EXAMPLE 90

A powdery composition is obtained as follows. Mix the following ingredients in the amounts specified.

| Ingredient | Weight Percent |
| --- | --- |
| Benzoyl peroxide (micronized) | 1 to 35 |
| calcium phosphate | 63 to 98.5 |
| cephalothin | 0.5 to 5 |

EXAMPLE 91

A liquid composition is obtained as follows. Mix the following ingredients in the amounts specified.

| Ingredient | Weight Percent |
| --- | --- |
| cephalothin | 0.5 to 5 |
| Benzoyl peroxide (micronized) | 1 to 30 |
| Ethanol | The Balance to 100% |

EXAMPLE 92

A topical dermatological composition containing cephalothin is obtained as follows. Mix the following ingredients in the amounts specified.

| Ingredient | Weight Percent |
| --- | --- |
| Ethyl alcohol | 48.0 |
| laureth-4 | 0.5 |

-continued

| Ingredient | Weight Percent |
| --- | --- |
| Isopropyl alcohol | 4.0 |
| Propylene glycol | 10.0 |
| cephalothin | 1.0 |
| Purified water | balance |

Citric acid can be used to adjust the pH to a desired level.

The composition in this example contains approximately 1% cephalothin. Other suitable compositions can be made in accordance with this example which include cephalothin in the following percentages: 0.5%, 2%, 3%, 4%, 5%, and 10%.

For Example 93, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 93, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 93

A topical dermatological gel composition containing cephalothin antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cephalothin (approximately 3 grams of cephalothin). The contents of the first container and the contents of the second container are stable for long periods of time. When the topical composition containing cephalothin and benzoyl peroxide of the invention is to be made, a quantity of 70% ethyl alcohol (e. g. 3 ml.) is added to the second container to dissolve the cephalothin and form an alcoholic solution thereof. Then the alcoholic solution of cephalothin is added to the first container, and all the ingredients are mixed to form the topical gel composition of the invention which contains both cephalothin and benzoyl peroxide. This composition of the invention is stable, under refrigeration, for approximately 3 months.

More specifically, the blended topical gel composition of the invention with contains cephalothin and benzoyl peroxide in a gel carrier or vehicle has the following components in the approximate amounts specified.

| Ingredient | Weight Percent |
| --- | --- |
| cephalothin | 3.0 |
| Benzoyl peroxide | 5.0 |
| Gel carrier or vehicle | 92.0 |

Citric acid can be used to adjust the pH to a desired level.

The composition in Example 93 contains approximately 3% cephalothin. Other suitable compositions can be made in accordance with Example 93 which include cephalothin in the following percentages: 0.5%, 1%, 2%, 4%, 5%, and 10%.

EXAMPLE 94

A dermatological lotion containing cephalothin is obtained by mixing the following ingredients in the amounts specified. The ingredients in Container A is blended with the ingredients in Container B.

| Ingredient | Weight Percent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cephalothin | 3.00 |

Citric acid can be used to adjust the pH to a desired level.

To obtain the lotion composition in this example, the composition in Container A is prepared. This composition in Container A is stable for long periods of time.

Container B can contain only cephalothin for a long period of time. Just prior to forming the complete lotion composition, 3 grams of acetone are added to Container B to dissolve the cephalothin. Then, the contents of Container A and Container B are combined to form the complete lotion composition of the invention.

The composition in this example contains approximately 3% cephalothin. Other suitable compositions can be made in accordance with Example 62 which include cephalothin in the following percentages: 0.5%, 1%, 2%, 4%, 5%, and 10%.

EXAMPLE 95

A lotion composition is obtained as follows. Mix the following ingredients in the amounts specified.

| Ingredient | Weight Percent |
| --- | --- |
| Ethoxylated cetyl-stearyl alcohol | 7 |

| Ingredient | Weight Percent |
| --- | --- |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cephalothin | 2 |

Other suitable compositions can be made in accordance with this example which include cephalothin in the following percentages: 0.5%, 1%, 3%, 4%, 5%, and 10%.

EXAMPLE 96

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalothin | 3 |

Other suitable compositions can be made in accordance with this example which include cephalothin in the following percentages: 0.5%, 1%, 2%, 4%, 5%, and 10%.

EXAMPLE 97

A cream composition is obtained as follows. Mix the following ingredients in the amounts specified.

| Ingredient | Weight Percent |
| --- | --- |
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalothin | 3 |

Other suitable compositions can be made in accordance with this example which include cephalothin in the following percentages: 0.5%, 1%, 2%, 4%, 5%, and 10%.

EXAMPLE 98

A gel composition is obtained as follows. Mix the following ingredients in the amounts specified.

| Ingredient | Weight Percent |
| --- | --- |
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cephalothin | 3 |

Other suitable compositions can be made in accordance with this example which include cephalothin in the following percentages: 0.5%, 1%, 2%, 4%, 5%, and 10%.

EXAMPLE 99

A suspension composition is obtained as follows. Mix the following ingredients in the amounts specified.

| Ingredient | Weight Percent |
| --- | --- |
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cephalothin | 2 |

Other suitable compositions can be made in accordance with this example which include cephalothin in the following percentages: 0.5%, 1%, 3%, 4%, 5%, and 10%.

EXAMPLE 100

A dermatological lotion is obtained by mixing the following ingredients in suitable amounts: cephalothin (approximately 1% by weight); and a carrier which includes isopropyl alcohol (approximately 80% by weight), purified water (approximately 9% by weight), and propylene glycol (approximately 10% by weight).

EXAMPLE 101

An oil-in-water emulsion containing cephalothin in ointment form is obtained as follows.

Part A is comprised of a 3.33% aqueous solution of cephalothin.

Part B is an ointment base comprised of:

| Ingredient | Weight Percent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cephalothin. Other suitable compositions can be made in accordance with this example which include cephalothin in the following percentages: 0.5%, 1%, 3%, 4%, 5%, and 10%.

EXAMPLE 102

A mineral-oil-based cephalothin ointment is obtained as follows.

Part A is comprised of a 6.66% aqueous solution of cephalothin.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cephalothin. Other suitable compositions can be made in accordance with this example which include cephalothin in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3% +6.86%). It is also noted that the combined weight percentages of the water and water-miscible alcohols is approximately 42.2% (31% +11.2%).

EXAMPLE 103

A topical dermatological composition containing cephalosporin C is obtained as follows. Mix the following ingredients in the amounts specified.

| Ingredient | Weight Percent |
| --- | --- |
| Ethyl alcohol | 41.5 |
| laureth-4 | 0.5 |
| Isopropyl alcohol | 6.0 |
| cephalosporin C | 2.0 |
| Purified water | balance |

Citric acid can be used to adjust the pH to a desired level.

The composition in this example contains approximately 2% cephalosporin C. Other suitable compositions can be made in accordance with this example which include cephalosporin C in the following percentages: 0.5%, 1%, 3%, 4%, 5%, and 10%.

EXAMPLE 104

A topical dermatological composition containing cephalosporin C is obtained as follows. Mix the following ingredients in the amounts specified.

| Ingredient | Weight Percent |
| --- | --- |
| Ethyl alcohol | 71.2 |
| Propylene glycol | 26.8 |
| cephalosporin C | 2.0 |

The composition in this example contains approximately 2% cephalosporin C.

Other topical dermatological compositions are presented below.

EXAMPLE 105

A formulation employing a water soluble gel as a carrier is obtained as follows. More details of the gel carrier are described in U.S. Pat. No. 4,837,378, incorporated herein by reference.

A 30 kilogram batch of a composition of the present invention containing cephalosporin C (as 0.75% by weight) is prepared as follows. 180 grams of Carbopol 940 TM (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cephalosporin C dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cephalosporin C in the following percentages: 0.5%, 1%, 2%, 3%, 4%, 5%, and 10%.

EXAMPLE 106

Another topical dermatological gel is obtained by mixing the following ingredients in suitable amounts: allantoin, carbomer 934P, methylparaben, polyethylene glycol 400, propylene glycol, sodium hydroxide, purified water and cephalosporin C.

EXAMPLE 107

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |

-continued

| Ingredient | Weight Percent |
| --- | --- |
| cephalosporin C | 0.5 to 5 |

EXAMPLE 108

A liquid composition is obtained as follows. Mix the following ingredients in the amounts specified.

| Ingredient | Weight Percent |
| --- | --- |
| cephalosporin C | 0.5 to 5 |
| Benzoyl peroxide (micronized) | 1 to 30 |
| Ethanol | The Balance to 100% |

EXAMPLE 109

A topical dermatological composition containing cephalosporin C is obtained as follows. Mix the following ingredients in the amounts specified.

| Ingredient | Weight Percent |
| --- | --- |
| Ethyl alcohol | 48.0 |
| laureth-4 | 0.5 |
| Isopropyl alcohol | 4.0 |
| Propylene glycol | 10.0 |
| cephalosporin C | 1.0 |
| Purified water | balance |

Citric acid can be used to adjust the pH to a desired level.

The composition in this example contains approximately 1% cephalosporin C. Other suitable compositions can be made in accordance with this example which include cephalosporin C in the following percentages: 0.5%, 2%, 3%, 4%, 5%, and 10%.

For Example 110, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 110, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |

-continued

| Ingredient in gel carrier | Weight Percent in the Final Mixture containing antibiotic, benzoyl peroxide, and gel carrier |
| --- | --- |
| Dioctyl sodium sulfosuccinate | 1.00 |

EXAMPLE 110

A topical dermatological gel composition containing cephalosporin C antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cephalosporin C (approximately 3 grams of cephalosporin C). The contents of the first container and the contents of the second container are stable for long periods of time. When the topical composition containing cephalosporin C and benzoyl peroxide of the invention is to be made, a quantity of 70% ethyl alcohol (e. g. 3 ml.) is added to the second container to dissolve the cephalosporin C and form an alcoholic solution thereof. Then the alcoholic solution of cephalosporin C is added to the first container, and all the ingredients are mixed to form the topical gel composition of the invention which contains both cephalosporin C and benzoyl peroxide. This composition of the invention is stable, under refrigeration, for approximately 3 months.

More specifically, the blended topical gel composition of the invention with contains cephalosporin C and benzoyl peroxide in a gel carrier or vehicle has the following components in the approximate amounts specified.

| Ingredient | Weight Percent |
| --- | --- |
| cephalosporin C | 3.0 |
| Benzoyl peroxide | 5.0 |
| Gel carrier or vehicle | 92.0 |

Citric acid can be used to adjust the pH to a desired level.

The composition in Example 110 contains approximately 3% cephalosporin C. Other suitable compositions can be made in accordance with Example 110 which include cephalosporin C in the following percentages: 0.5%, 1%, 2%, 4%, 5%, and 10%.

EXAMPLE 111

A dermatological lotion containing cephalosporin C is obtained by mixing the following ingredients in the amounts specified. The ingredients in Container A is blended with the ingredients in Container B.

| Ingredient | Weight Percent of ingredient in overall lotion |
| --- | --- |
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |

-continued

| Ingredient | Weight Percent of ingredient in overall lotion |
|---|---|
| Acetone | 7.00 |
| Dioctyl sodium sulfosuccinate | 0.10 |
| In Container B: | |
| Acetone | 3.00 |
| cephalosporin C | 3.00 |

Citric acid can be used to adjust the pH to a desired level.

To obtain the lotion composition in this example, the composition in Container A is prepared. This composition in Container A is stable for long periods of time.

Container B can contain only cephalosporin C for a long period of time. Just prior to forming the complete lotion composition, 3 grams of acetone are added to Container B to dissolve the cephalosporin C. Then, the contents of Container A and Container B are combined to form the complete lotion composition of the invention.

The composition in this example contains approximately 3% cephalosporin C. Other suitable compositions can be made in accordance with Example 62 which include cephalosporin C in the following percentages: 0.5%, 1%, 2%, 4%, 5%, and 10%.

EXAMPLE 112

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cephalosporin C | 2 |

Other suitable compositions can be made in accordance with this example which include cephalosporin C in the following percentages: 0.5%, 1%, 3%, 4%, 5%, and 10%.

EXAMPLE 113

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalosporin C | 3 |

Other suitable compositions can be made in accordance with this example which include cephalosporin C in the following percentages: 0.5%, 1%, 2%, 4%, 5%, and 10%.

EXAMPLE 114

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cephalosporin C | 3 |

Other suitable compositions can be made in accordance with this example which include cephalosporin C in the following percentages: 0.5%, 1%, 3%, 4%, 5%, and 10%.

EXAMPLE 115

A gel composition is obtained as follows. Mix the following ingredients in the amounts specified.

| Ingredient | Weight Percent |
|---|---|
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cephalosporin C | 3 |

Other suitable compositions can be made in accordance with this example which include cephalosporin C in the following percentages: 0.5%, 1%, 2%, 4%, 5%, and 10%.

EXAMPLE 116

A suspension composition is obtained as follows. Mix the following ingredients in the amounts specified.

| Ingredient | Weight Percent |
|---|---|
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cephalosporin C | 2 |

Other suitable compositions can be made in accordance with this example which include cephalosporin C in the following percentages: 0.5%, 1%, 3%, 4%, 5%, and 10%.

EXAMPLE 117

A dermatological lotion is obtained by mixing the following ingredients in suitable amounts: cephalosporin C (approximately 1% by weight); and a carrier which includes isopropyl alcohol (approximately 80% by weight), purified water (approximately 9% by weight), and propylene glycol (approximately 10% by weight).

EXAMPLE 118

An oil-in-water emulsion containing cephalosporin C in ointment form is obtained as follows.

Part A is comprised of a 3.33% aqueous solution of cephalosporin C.

Part B is an ointment base comprised of:

| Ingredient | Weight Percent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cephalosporin C. Other suitable compositions can be made in accordance with this example which include cephalosporin C in the following percentages: 0.5%, 1%, 3%, 4%, 5%, and 10%.

EXAMPLE 119

A mineral-oil-based cephalosporin C ointment is obtained as follows.

Part A is comprised of a 6.66% aqueous solution of cephalosporin C.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cephalosporin C. Other suitable compositions can be made in accordance with this example which include cephalosporin C in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34 %) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 120

A topical dermatological composition containing cefoperazone is obtained as follows. Mix the following ingredients in the amounts specified.

| Ingredient | Weight Percent |
|---|---|
| Ethyl alcohol | 41.5 |
| laureth-4 | 0.5 |
| Isopropyl alcohol | 6.0 |
| cefoperazone | 2.0 |
| Purified water | balance |

Citric acid can be used to adjust the pH to a desired level.

The composition in this example contains approximately 2% cefoperazone. Other suitable compositions can be made in accordance with this example which include cefoperazone in the following percentages: 0.5%, 1%, 3%, 4%, 5%, and 10%.

EXAMPLE 121

A topical dermatological composition containing cefoperazone is obtained as follows. Mix the following ingredients in the amounts specified.

| Ingredient | Weight Percent |
|---|---|
| Ethyl alcohol | 71.2 |
| Propylene glycol | 26.8 |
| cefoperazone | 2.0 |

The composition in this example contains approximately 2% cefoperazone.

Other topical dermatological compositions are presented below.

EXAMPLE 122

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefoperazone (as 0.75% by weight) is prepared as follows. 180 grams of Carbopol 940 ™ (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefoperazone dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefoperazone in the following percentages: 0.5%, 1%, 2%, 3%, 4%, 5%, and 10%.

EXAMPLE 123

Another topical dermatological gel is obtained by mixing the following ingredients in suitable amounts: allantoin, carbomer 934P, methylparaben, polyethylene glycol 400, propylene glycol, sodium hydroxide, purified water and cefoperazone.

EXAMPLE 124

A powdery composition is obtained as follows. Mix the following ingredients in the amounts specified.

| Ingredient | Weight Percent |
| --- | --- |
| Benzoyl peroxide (micronized) | 1 to 35 |
| Calcium phosphate | 63 to 98.5 |
| cefoperazone | 0.5 to 5 |

EXAMPLE 125

A liquid composition is obtained as follows. Mix the following ingredients in the amounts specified.

| Ingredient | Weight Percent |
| --- | --- |
| cefoperazone | 0.5 to 5 |
| Benzoyl peroxide (micronized) | 1 to 30 |
| Ethanol | The Balance to 100% |

EXAMPLE 126

A topical dermatological composition containing cefoperazone is obtained as follows. Mix the following ingredients in the amounts specified.

| Ingredient | Weight Percent |
| --- | --- |
| Ethyl alcohol | 48.0 |
| laureth-4 | 0.5 |
| Isopropyl alcohol | 4.0 |
| Propylene glycol | 10.0 |
| cefoperazone | 1.0 |
| Purified water | balance |

Citric acid can be used to adjust the pH to a desired level.

The composition in this example contains approximately 1% cefoperazone. Other suitable compositions can be made in accordance with this example which include cefoperazone in the following percentages: 0.5%, 2%, 3%, 4%, 5%, and 10%.

For Example 127, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 127, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 127

A topical dermatological gel composition containing cefoperazone antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefoperazone (approximately 3 grams of cefoperazone). The contents of the first container and the contents of the second container are stable for long periods of time. When the topical composition containing cefoperazone and benzoyl peroxide of the invention is to be made, a quantity of 70% ethyl alcohol (e. g. 3 ml.) is added to the second container to dissolve the cefoperazone and form an alcoholic solution thereof. Then the alcoholic solution of cefoperazone is added to the first container, and all the ingredients are mixed to form the topical gel composition of the invention which contains both cefoperazone and benzoyl peroxide. This composition of the invention is stable, under refrigeration, for approximately 3 months.

More specifically, the blended topical gel composition of the invention with contains cefoperazone and benzoyl peroxide in a gel carrier or vehicle has the following components in the approximate amounts specified.

| Ingredient | Weight Percent |
| --- | --- |
| cefoperazone | 3.0 |
| Benzoyl peroxide | 5.0 |
| Gel carrier or vehicle | 92.0 |

Citric acid can be used to adjust the pH to a desired level.

The composition in Example 127 contains approximately 3% cefoperazone. Other suitable compositions can be made in accordance with Example 127 which include cefoperazone in the following percentages: 0.5%, 1%, 2%, 4%, 5%, and 10%.

EXAMPLE 128

A dermatological lotion containing cefoperazone is obtained by mixing the following ingredients in the amounts specified. The ingredients in Container A is blended with the ingredients in Container B.

| Ingredient | Weight Percent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cefoperazone | 3.00 |

Citric acid can be used to adjust the pH to a desired level.

To obtain the lotion composition in this example, the composition in Container A is prepared. This composition in Container A is stable for long periods of time.

Container B can contain only cefoperazone for a long period of time. Just prior to forming the complete lotion composition, 3 grams of acetone are added to Container B to dissolve the cefoperazone. Then, the contents of Container A and Container B are combined to form the complete lotion composition of the invention.

The composition in this example contains approximately 3% cefoperazone. Other suitable compositions can be made in accordance with Example 62 which include cefoperazone in the following percentages: 0.5%, 1%, 2%, 4%, 5%, and 10%.

EXAMPLE 129

A lotion composition is obtained as follows. Mix the following ingredients in the amounts specified.

| Ingredient | Weight Percent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefoperazone | 2 |

Other suitable compositions can be made in accordance with this example which include cefoperazone in the following percentages: 0.5%, 1%, 3%, 4%, 5%, and 10%.

EXAMPLE 130

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefoperazone | 3 |

Other suitable compositions can be made in accordance with this example which include cefoperazone in the following percentages: 0.5%, 1%, 2%, 4%, 5%, and 10%.

EXAMPLE 131

A cream composition is obtained as follows. Mix the following ingredients in the amounts specified.

| Ingredient | Weight Percent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefoperazone | 3 |

Other suitable compositions can be made in accordance with this example which include cefoperazone in the following percentages: 0.5%, 1%, 2%, 4%, 5%, and 10%.

EXAMPLE 132

A gel composition is obtained as follows. Mix the following ingredients in the amounts specified.

| Ingredient | Weight Percent |
|---|---|
| Water, deionized or distilled | 51.65 |
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cefoperazone | 3 |

Other suitable compositions can be made in accordance with this example which include cefoperazone in the following percentages: 0.5%, 1%, 2%, 4%, 5%, and 10%.

EXAMPLE 133

A suspension composition is obtained as follows. Mix the following ingredients in the amounts specified.

| Ingredient | Weight Percent |
|---|---|
| Water, deionized or distilled | 54.97 |
| Butylated hydroxyanisole | 0.10 |
| Benzoyl peroxide (micronized) | 5 |

-continued

| Ingredient | Weight Percent |
| --- | --- |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cefoperazone | 2 |

Other suitable compositions can be made in accordance with this example which include cefoperazone in the following percentages: 0.5%, 1%, 3%, 4%, 5%, and 10%.

EXAMPLE 134

A dermatological lotion is obtained by mixing the following ingredients in suitable amounts: cefoperazone (approximately 1% by weight); and a carrier which includes isopropyl alcohol (approximately 80% by weight), purified water (approximately 9% by weight), and propylene glycol (approximately 10% by weight).

EXAMPLE 135

An oil-in-water emulsion containing cefoperazone in ointment form is obtained as follows.

Part A is comprised of a 3.33% aqueous solution of cefoperazone.

Part B is an ointment base comprised of:

| Ingredient | Weight Per Cent |
| --- | --- |
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefoperazone. Other suitable compositions can be made in accordance with this example which include cefoperazone in the following percentages: 0.5%, 1%, 3%, 4%, 5%, and 10%.

EXAMPLE 136

A mineral-oil-based cefoperazone ointment is obtained as follows.

Part A is comprised of a 6.66% aqueous solution of cefoperazone.

Part B is an ointment base comprised of:

| Ingredient | Parts |
| --- | --- |
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefoperazone. Other suitable compositions can be made in accordance with this example which include cefoperazone in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g. ×6.66%) and approximately 28 grams of water (30 g. ×93.34%) are obtained.

By taking 70 ml. of part B, approximately 3.9 grams of isopropyl alcohol (5 ml. ×0.78 g/ml.), approximately 6.25 grams of glycerin (5 ml. ×1.25 g/ml.), and approximately 51 grams of mineral oil (60 ml. ×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 137

A topical dermatological composition containing cefotaxime is obtained as follows. Mix the following ingredients in the amounts specified.

| Ingredient | Weight Per Cent |
| --- | --- |
| Ethyl alcohol | 41.5 |
| laureth-4 | 0.5 |
| Isopropyl alcohol | 6.0 |
| cefotaxime | 2.0 |
| Purified water | balance |

Citric acid can be used to adjust the pH to a desired level.

The composition in this example contains approximately 2% cefotaxime. Other suitable compositions can be made in accordance with this example which include cefotaxime in the following percentages: 0.5%, 1%, 3%, 4%, 5%, and 10%.

EXAMPLE 138

A topical dermatological composition containing cefotaxime is obtained as follows. Mix the following ingredients in the amounts specified.

| Ingredient | Weight Per Cent |
| --- | --- |
| Ethyl alcohol | 71.2 |
| Propylene glycol | 26.8 |
| cefotaxime | 2.0 |

The composition in this example contains approximately 2% cefotaxime.

Other topical dermatological compositions are presented below.

EXAMPLE 139

A formulation employing a water soluble gel as a carrier is obtained as follows. More details of the gel carrier are described in U.S. Pat. No. 4,837,378, incorporated herein by reference.

A 30 kilogram batch of a composition of the present invention containing cefotaxime (as 0.75% by weight) is prepared as follows. 180 grams of Carbopol 940 ™ (0.6% by weight of the final weight of the composition) was dissolved in 16.5 liters of distilled water containing 15 grams of ethylenediaminetetraacetic acid (EDTA) disodium dihydrate. Sufficient amount of 10 wt % sodium hydroxide (NaOH) solution is added to bring the pH value to about 5. This aqueous polymer solution is called "Part A". "Part B" is prepared by mixing 900 grams of propylene glycol (3% by weight of the final weight of the composition), 24 grams of methyl paraben (0.08% by weight of the final weight of the composition), and 6.0 grams of propyl paraben (0.02% by weight of the final weight of the composition). The mixture is added to 225 grams of cefotaxime dispersed in 11.4 liters of distilled water maintained at 50 degrees Centigrade. Parts A and B are then mixed thoroughly and gelling of the composition results. A cold aqueous solution of NaOH is then used to adjust the final pH value to approximately 5.25. Distilled water is then added to give the desired 30 kilogram final weight. The NaOH and water are thoroughly mixed into a viscous gel. Other suitable compositions can be made in accordance with this example which include cefotaxime in the following percentages: 0.5%, 1%, 2%, 3%, 4%, 5%, and 10%.

EXAMPLE 140

Another topical dermatological gel is obtained by mixing the following ingredients in suitable amounts: allantoin, carbomer 934P, methylparaben, polyethylene glycol 400, propylene glycol, sodium hydroxide, purified water and cefotaxime.

EXAMPLE 141

A powdery composition is obtained as follows. Mix the following ingredients in the amounts specified.

| Ingredient | Weight Per Cent |
| --- | --- |
| Benzoyl peroxide (micronized) | 1 to 35 |
| Calcium phosphate | 63 to 98.5 |
| cefotaxime | 0.5 to 5 |

EXAMPLE 142

A liquid composition is obtained as follows. Mix the following ingredients in the amounts specified.

| Ingredient | Weight Per Cent |
| --- | --- |
| cefotaxime | 0.5 to 5 |
| Benzoyl peroxide (micronized) | 1 to 30 |
| Ethanol | The Balance to 100% |

EXAMPLE 143

A topical dermatological composition containing cefotaxime is obtained as follows. Mix the following ingredients in the amounts specified.

| Ingredient | Weight Per Cent |
| --- | --- |
| Ethyl alcohol | 48.0 |
| laureth-4 | 0.5 |
| Isopropyl alcohol | 4.0 |
| Propylene glycol | 10.0 |
| cefotaxime | 1.0 |
| Purified water | balance |

Citric acid can be used to adjust the pH to a desired level.

The composition in this example contains approximately 1% cefotaxime. Other suitable compositions can be made in accordance with this example which include cefotaxime in the following percentages: 0.5%, 2%, 3%, 4%, 5%, and 10%.

For Example 144, reference is made to U.S. Pat. No. 4,497,794, incorporated herein by reference, in which topical gel compositions containing the antibiotic erythromycin and benzoyl peroxide in a gel carrier are disclosed. A number of topical gel compositions of the present invention can be made by simply replacing the erythromycin disclosed in the gel compositions in said patent with a cephalosporin to provide topical gel compositions of the invention which contain benzoyl peroxide and the respective cephalosporin antibiotic of the invention.

The gel carrier or vehicle for Example 144, prior to addition of the benzoyl peroxide and prior to addition of the respective cephalosporin antibiotic of the invention and, as explained below, the approximately 3 ml. of ethyl alcohol used to dissolve the respective antibiotic for addition to the gel carrier to which benzoyl peroxide has been added, is comprised of the following ingredients in the approximate amounts specified.

| Ingredient in gel carrier | Weight Percent in the Final Mixture containing antibiotic, benzoyl peroxide, and gel carrier |
| --- | --- |
| Butylated hydroxyanisole | 0.10 |
| Colloidal Bentonite | 2.50 |
| Carboxy vinyl polymer (acid form) | 1.00 |
| Water, deionized or distilled | 54.65 |
| Diisopropanolamine | 0.75 |
| Ethyl alcohol | 32.00 |
| Dioctyl sodium sulfosuccinate | 1.00 |

EXAMPLE 144

A topical dermatological gel composition containing cefotaxime antibiotic and benzoyl peroxide in a gel carrier or vehicle is obtained as follows.

To a first container add the benzoyl peroxide and the gel carrier or vehicle ingredients (approximately 5 grams of benzoyl peroxide and approximately 89 grams of gel carrier or vehicle). To a second container add powdered cefotaxime (approximately 3 grams of cefotaxime). The contents of the first container and the contents of the second container are stable for long periods of time. When the topical composition containing cefotaxime and benzoyl peroxide of the invention is to be made, a quantity of 70% ethyl alcohol (e. g. 3 ml.) is added to the second container to dissolve the cefotaxime and form an alcoholic solution thereof. Then the alcoholic solution of cefotaxime is added to the first container, and all the ingredients are mixed to form the topical gel composition of the invention which contains both cefotaxime and benzoyl peroxide. This composition of the invention is stable, under refrigeration, for approximately 3 months.

More specifically, the blended topical gel composition of the invention with contains cefotaxime and benzoyl peroxide in a gel carrier or vehicle has the following components in the approximate amounts specified.

| Ingredient | Weight Per Cent |
|---|---|
| cefotaxime | 3.0 |
| Benzoyl peroxide | 5.0 |
| Gel carrier or vehicle | 92.0 |

Citric acid can be used to adjust the pH to a desired level.

The composition in Example 144 contains approximately 3% cefotaxime. Other suitable compositions can be made in accordance with Example 144 which include cefotaxime in the following percentages: 0.5%, 1%, 2%, 4%, 5%, and 10%.

EXAMPLE 145

A dermatological lotion containing cefotaxime is obtained by mixing the following ingredients in the amounts specified. The ingredients in Container A is blended with the ingredients in Container B.

| Ingredient | Weight Per Cent of ingredient in overall lotion |
|---|---|
| In Container A: | |
| Ethoxylated cetyl-stearyl alcohol | 7.00 |
| Cetyl alcohol | 0.75 |
| Isopropyl myristate | 5.00 |
| Butylated hydroxyanisole | 0.10 |
| Polyoxyl 40 stearate | 0.25 |
| Water, deionized or distilled | 70.80 |
| Propylene glycol | 3.00 |
| Acetone | 7.00 |
| Dioctyl sodium sulfosuccinate | 0.10 |
| In Container B: | |
| Acetone | 3.00 |
| cefotaxime | 3.00 |

Citric acid can be used to adjust the pH to a desired level.

To obtain the lotion composition in this example, the composition in Container A is prepared. This composition in Container A is stable for long periods of time.

Container B can contain only cefotaxime for a long period of time. Just prior to forming the complete lotion composition, 3 grams of acetone are added to Container B to dissolve the cefotaxime. Then, the contents of Container A and Container B are combined to form the complete lotion composition of the invention.

The composition in this example contains approximately 3% cefotaxime. Other suitable compositions can be made in accordance with Example 62 which include cefotaxime in the following percentages: 0.5%, 1%, 2%, 4%, 5%, and 10%.

EXAMPLE 146

A lotion composition is obtained as follows. Mix the following ingredients in the amounts specified.

| Ingredient | Weight Per Cent |
|---|---|
| Ethoxylated cetyl-stearyl alcohol | 7 |
| Cetyl alcohol | 0.75 |
| Isostearyl neopentanoate | 5 |
| Butylated hydroxyanisole | 0.10 |
| Polyoxyl 40 stearate | 0.25 |
| Water, deionized or distilled | 66.8 |
| Propylene glycol | 3 |
| Benzoyl peroxide (micronized) | 5 |
| Acetone | 10 |
| Dioctyl sodium sulphosuccinate | 0.1 |
| cefotaxime | 2 |

Other suitable compositions can be made in accordance with this example which include cefotaxime in the following percentages: 0.5%, 1%, 3%, 4%, 5%, and 10%.

EXAMPLE 147

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Isostearyl neopentanoate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefotaxime | 3 |

Other suitable compositions can be made in accordance with this example which include cefotaxime in the following percentages: 0.5%, 1%, 2%, 4%, 5%, and 10%.

EXAMPLE 148

A cream composition is obtained as follows. Mix the following ingredients in the amounts specified.

| Ingredient | Weight Per Cent |
|---|---|
| Ethoxylated cetyl-stearyl alcohol | 15 |
| Cetyl alcohol | 1.25 |
| Decyl oleate | 5 |
| Butylated hydroxyanisole | 0.10 |
| Polyoxyl 40 stearate | 0.25 |
| Water, deionized or distilled | 57.30 |
| Propylene glycol | 3 |
| Benzoyl peroxide (micronized) | 5 |
| Acetone | 10 |
| Dioctyl sodium sulphosuccinate | 0.1 |
| cefotaxime | 3 |

Other suitable compositions can be made in accordance with this example which include cefotaxime in the following percentages: 0.5%, 1%, 2%, 4%, 5%, and 10%.

EXAMPLE 149

A gel composition is obtained as follows. Mix the following ingredients in the amounts specified.

| Ingredient | Weight Per Cent |
|---|---|
| Water, deionized or distilled | 51.65 |

| Ingredient | Weight Per Cent |
|---|---|
| Butylated hydroxyanisole | 0.10 |
| Benzoyl peroxide (micronized) | 5 |
| Dioctyl sodium sulphosuccinate | 1 |
| Colloidal Bentonite | 2.5 |
| Carboxy vinyl polymer (acid form) | 1 |
| Ethyl alcohol | 35 |
| Diisopropanolamine | 0.75 |
| cefotaxime | 3 |

Other suitable compositions can be made in accordance with this example which include cefotaxime in the following percentages: 0.5%, 1%, 2%, 4%, 5%, and 10%.

EXAMPLE 150

A suspension composition is obtained as follows. Mix the following ingredients in the amounts specified.

| Ingredient | Weight Per Cent |
|---|---|
| Water, deionized or distilled | 54.97 |
| Butylated hydroxyanisole | 0.10 |
| Benzoyl peroxide (micronized) | 5 |
| Dioctyl sodium sulphosuccinate | 1 |
| Colloidal Bentonite | 1.5 |
| Carboxy vinyl polymer (acid form) | 0.25 |
| Ethyl alcohol | 35 |
| Diisopropanolamine | 0.18 |
| cefotaxime | 2 |

Other suitable compositions can be made in accordance with this example which include cefotaxime in the following percentages: 0.5%, 1%, 3%, 4%, 5%, and 10%.

EXAMPLE 151

A dermatological lotion is obtained by mixing the following ingredients in suitable amounts: cefotaxime (approximately 1% by weight); and a carrier which includes isopropyl alcohol (approximately 80% by weight), purified water (approximately 9% by weight), and propylene glycol (approximately 10% by weight).

EXAMPLE 152

An oil-in-water emulsion containing cefotaxime in ointment form is obtained as follows.

Part A is comprised of a 3.33% aqueous solution of cefotaxime.

Part B is an ointment base comprised of:

| Ingredient | Weight Per Cent |
|---|---|
| viscid paraffin | 35 |
| white vaseline | 35 |
| cetylstearyl alcohol | 30 |

A mixture is obtained as follows. Mix 60 ml. of Part A is mixed with 40 ml. of Part B to provide an oil-in-water emulsion in ointment form containing approximately 2% cefotaxime. Other suitable compositions can be made in accordance with this example which include cefotaxime in the following percentages: 0.5%, 1%, 3%, 4%, 5%, and 10%.

EXAMPLE 153

A mineral-oil-based cefotaxime ointment is obtained as follows.

Part A is comprised of a 6.66% aqueous solution of cefotaxime.

Part B is an ointment base comprised of:

| Ingredient | Parts |
|---|---|
| glycerin | 5 |
| isopropyl alcohol, 96% | 5 |
| mineral oil | 60 |

A mixture is obtained as follows. Mix 30 ml. of Part A with 70 ml. of Part B to provide a mineral-oil-based ointment containing approximately 2% cefotaxime. Other suitable compositions can be made in accordance with this example which include cefotaxime in the following percentages: 0.5%, 1%, 3%, 4%, 5%, and 10%.

From the volumes in this example, it is easy to convert to approximate weight percents. To make the conversion, certain inherent properties of water, isopropyl alcohol, glycerin, and mineral oil are employed. More specifically, to make the conversion to approximate weight percents, the known densities of water, isopropyl alcohol, glycerin, and mineral oil are employed. The known density of water is approximately 1 g/ml. The known density of isopropyl alcohol is approximately 0.78 g/ml. The known density of glycerin is approximately 1.25 g/ml. The known density of mineral oil is approximately 0.85 g/ml.

The weight of the 30 ml. of part A is approximately 30 grams, in view of the fact that part A is predominately water. By taking 30 ml. of part A, approximately 2 grams of antibiotic (30 g.×6.66%) and approximately 28 grams of water (30 g.×93.34%) are obtained.

By taking 70 ml. of part B, approximately 3.9 grams of isopropyl alcohol (5 ml.×0.78 g/ml.), approximately 6.25 grams of glycerin (5 ml.×1.25 g/ml.), and approximately 51 grams of mineral oil (60 ml.×0.85 g/ml.) are obtained. The weight of 70 ml. of part B is approximately 61.15 grams (3.9 g.+6.25 g.+51 g.).

Therefore, the total weight of parts A and B combined is approximately 91.15 grams (30 g.+61.15 g.).

In the combination of parts A and B, the weight percents of the individual carrier components are as approximately as follows: water, 31%; isopropyl alcohol, 4.3%; glycerin, 6.86%; and mineral oil, 55.95%. It is noted that the combined weight percentages of the water-miscible alcohols is approximately 11.2% (4.3%+6.86%). It is also noted that the combined weight percentages of the water and water-miscible alcohols is approximately 42.2% (31%+11.2%).

EXAMPLE 154

There is a well known and commercially available liquid-absorbed wipe known as Erycette TM which is a 2% erythromycin topical solution absorbed into a wipe material comprised of fibrous material. These wipes are packaged in individually sealed aluminum foil packets called Piedgets. As disclosed on the Pledget package, each milliliter of liquid absorbed on the cloth wipe contains 20 mgm erythromycin base in a vehicle consisting of alcohol (66%) and propylene glycol and may contain citric acid to adjust pH. Each pledget is filled to contain 0.8 ml. of solution.

Now in accordance with the principles of the present invention, a 2% cefaclor topical solution is prepared and is absorbed into a quantity of an absorbant wipe material comprised of fibrous material such as cloth, paper, or synthetic fibers. Alternatively, an open-cell foam absorbent material can be used. The wipes are packaged in individually sealed aluminum foil packets. Each milliliter of liquid absorbed on the wipe contains 20 mgm cefaclor base in a vehicle consisting of alcohol (66%) and propylene glycol and may contain citric acid to adjust pH. Each individual wipe is filled to contain 0.8 ml. of solution.

A variety of strengths can be used for the cefaclor solution in the liquid-absorbed wipe. For example, the cefaclor antibiotic can be present in a range spanning 0.5–10% by weight.

A variety of liquid carriers and a variety of strengths of the liquid carriers can be used for the cefaclor antibiotic. For example, the carrier can contain a quantity of water in addition to the alcohol and propylene glycol. Moreover, a carrier can contain a blend of water, ethyl alcohol, and isopropyl alcohol such as found in the carrier known as "Neutrogina Vehicle N (mild)" made by Neutrogena Dermatologics Division of Neutrogena Corporation, Los Angeles Corporation. A wide range of proportions of individual carrier ingredients can be employed. Further, in accordance with the principles of the present invention, a 2% cephalosporin topical solution is prepared and is absorbed into a quantity of an absorbant wipe material comprised of fibrous material such as cloth, paper, or synthetic fibers. Alternatively, an open-cell foam absorbent material can be used. The wipes are packaged in individually sealed aluminum foil packets. Each milliliter of liquid absorbed on the wipe contains 20 mgm cephalosporin base in a vehicle consisting of alcohol (66%) and propylene glycol and may contain citric acid to adjust pH. Each individual wipe is filled to contain 0.8 ml. of solution. A variety of strengths can be used for the cephalosporin solution in the liquid-absorbed wipe. For example, the cephalosporin antibiotic can be present in a range spanning 0.5–10% by weight. A variety of liquid carriers and a variety of strengths of the liquid carriers can be used for the cephalosporin antibiotic. For example, the carrier can contain a quantity of water in addition to the alcohol and propylene glycol. Moreover, a carrier can contain a blend of water, ethyl alcohol, and isopropyl alcohol such as found in the carrier known as "Neutrogina Vehicle N (mild)" made by Neutrogena Dermatologics Division of Neutrogena Corporation, Los Angeles Corporation. A wide range of proportions of individual carrier ingredients can be employed.

EXAMPLE 155

In this example, a cephalosporin is prepared for topical administration with liposomes. Methods of preparing liposomes containing active ingredients are disclosed in U.S. Pat. No. 4,673,567, incorporated herein by reference. More specifically, Examples 1 and 4 (which is for the cephalosporin cefalexin) in U.S. Pat. No. 4,673,567 are adapted herein for use with the cephalosporin cefaclor.

More specifically, 700 mg of D,L-dipalmitoylphosphatidyl choline is dissolved in chloroform in a round-bottom flask. The chloroform is removed by a rotary evaporator to form a thin layer of phospholipid on the inner wall of the round-bottom flask. The phospholipid is dried sufficiently under reduced pressure, to which 25 ml of water is added. The mixture is shaken by hand at 50 degrees Centigrade for about 7 minutes to give a dispersion of liposomes (multilamellar vesicles, MLV). The dispersion is frozen by the used of dry ice/acetone and dried by vacuum lyophilization. The powder obtained is collected and placed in a tube for centrifugal separation. A solution of cefaclor (2% cefaclor by weight) is dissolved in purified water in the tube; and 2-fold diluted aqueous isotonic sodium chloride solution and 0.02M phosphate buffer are added to the tube. The mixture is dispersed well, then warmed up and kept at 50 degrees Centigrade for five minutes and washed twice with an isotonic phosphate buffer solution (pH 7.4) at room temperature by means of ultra-centrifugal separation. The liposomes, containing the cefaclor, are dried by lyophilization and blended with purified water for topical administration to treat acne.

The cefaclor used can be in a solution in a range of 0.5% to 10% by weight. More generally, the cephalosporin can be in a solution in a range of 0.5% to 10% by weight.

The lyophilized powder which contains the cephalosporin in liposomes can also be used in creams and gels.

EXAMPLE 156

A time-release patch containing a cephalosporin is described below. The making of the time-release patch is adapted from U.S. Pat. No. 4,839,174, incorporated herein by reference, which discloses the making of nicotine patches. More specifically, Example 1 is adapted for use with a cephalosporin.

Monolithic patches containing the cephalosporin cefaclor are made as follows. A solution of cefaclor-loaded Pellethane 2363-80AE is made by mixing Pellethane pellets into tetrahydrofuran, adding cefaclor to be 2% by weight cefaclor. The mixture is agitated on a bottle roller for three days to form a matrix mixture. A layer of backing material grade 3M-1005 is spread in a petri dish and covered with the matrix mixture. The petri dish is covered, and the matrix is left to cure for 10 days at room temperature to form the time-release, cefaclor composition. Patches are cut from the finished matrix. Time-release patches can be made in a variety of sizes to accommodate different anatomic locations to which the patches are applied. The cefaclor can be added in a range spanning 0.5% to 20% by weight.

As mentioned above, a carrier for the cephalosporin can contain a blend of water, ethyl alcohol, and isopropyl alcohol such as found in the carrier known as "Neutrogina Vehicle N (mild)" made by Neutrogena Dermatologics Division of Neutrogena Corporation, Los Angeles Corporation. More generally, however, a broad range of suitable amounts of cephalosporin antibiotic and respective carrier ingredients is as follows: the cephalosporin antibiotic is present in an amount in a range of 0.5–5% by weight; the ethyl alcohol is present in a range of 35–50% by weight; the laureth-4 is present in a range of 0–1% by weight; the isopropyl alcohol is present in a range of 0–10% by weight; and the water is present in a range of 35–60% by weight.

Also, more generally with respect to a broad range of cephalosporin antibiotic used in combination with benzoyl peroxide active ingredient and a pharmaceutical carrier, the cephalosporin antibiotic can be present in an amount in a range of 0.5–5% by weight; the benzoyl peroxide can be present in an amount in a range of 3–10% by weight; and the carrier can be a gel vehicle present in an amount in a range of 85–96.5% by weight.

The detailed examples set forth above employ the following cephalosporins: cefaclor; cefoperazone; cefotaxime; cefotetan; cefuroxime; cephalexin; cephalosporin C; cephalothin; and cefuroxime-axetil.

Although not disclosed in detailed examples, the following cephalosporins can be prepared in compositions analogous to those cephalosporins disclosed above: cefadroxil; cefamandole nafate; cefazolin; cefmetazole; cefonicid; ceforanide; cefotanme; cefotixime; cefoxitin; cefpodoxime proxetil, ceftazidime; ceftizoxime; ceftriaxone; ceftriaxone moxalactam (a 1-oxabetalactam); cephalosporin C, sodium salt; cephalothin, sodium salt; cephapirin; cephradine; dihydratecephalothin; and moxalactam.

Three patients having acne vulgaris and one patient having acne rosacea have been successfully treated with 2% topical cephalosporin (cefaclor) designated as 3-chloro-7-D-(2-phenylglycinamido)-3-cephem-4-carboxylic acid, and the case histories are described as follows.

Patient number one is a female and began treatment at the age of 20 for acne vulgaris. She was first seen by one of the inventors, Dr. Howard Robinson, at age 23. However, prior to being seen by Dr. Robinson, she was seen in another city by another dermatologist who had prescribed oral minocycline, oral tetracycline, and topical 2% clindamycin solution. Over the course of six months prior to seeing Dr. Robinson, she had been treated with the following agents in the order specified: first, tretinoin, oral ampicillin 1 gm. per day, topical gentamicin cream, topical benzoyl peroxide, topical 2% sulfur, and 5% benzoyl peroxide; second, oral ampicillin 500 mgms. a day, topical tretinoin, topical gentamicin cream, and topical benzoyl peroxide; third, oral ampicillin 500 mgms. 1 week prior to menstrual cycle, topical gentamicin cream, and topical tretinoin. Then severity of the patient's acne worsened. Then photos were taken of the patient's face. The physical exam of the patient's face revealed 2+ comedones on a scale of 0-3+ and 2+ papules on a scale of 0-3+. It is noted that the scale used for describing the symptoms of acne herein is an adaptation of the scale described on page 611 of Bleicher, P., Charles, J., and Sober, A., "Topical Metronidazole Therapy for Rosacea", *Arch Dermatol*, 1987, Vol. 123, pages 609–614 Briefly, in the scale used, "0" is for an absence of lesions (papules, comedones, or pustules, respectively); "1+" is for mild lesions; "2+" is for moderate lesions; and "3+" is for severe lesions.

At this point, oral ampicillin was discontinued, topical gentamicin cream was discontinued, and topical tretinoin was discontinued. A 2% cefaclor was prepared in a vehicle known as "Neutrogina Vehicle N (mild)" made by Neutrogena Dermatologics Division of Neutrogena Corporation, Los Angeles Corporation. The overall composition of the 2% cefaclor composition contained approximately: cefaclor (2% by weight), ethyl alcohol (41.5% by weight), laureth-4 (0.5% by weight), isopropyl alcohol (6.0% by weight), and purified water (50.0% by weight). This 2% cefaclor composition was prescribed topically, in accordance with the invention, along with tretinoin topically. Approximately 5 weeks later, the patient subjectively indicated that her condition was improving. Also, at this time a physical examination was conducted which revealed on the face 1+ comedones and 1+ papules. This constituted a 50% improvement over a period of 5 weeks with the invention in contrast to negligible improvement with prior art treatment over the course of six months. Photos were taken.

The second patient is a female, first examined by Dr. Robinson at age 30 for the treatment of acne vulgaris. Prior to this examination, and over a period of 12 years, she was treated for acne vulgaris in a number of prior art ways. She had been treated over the last three years with: first, oral ampicillin (1 gm. per day), topical tretinoin, topical clindamycin; second, reduced oral ampicillin (500 mgm. per day) down to 1 week prior to her menstrual cycle, topical tretinoin, and topical clindamycin; third, increased oral ampicillin (1 gm. per day), and topical 2% erythromycin. Then, the patient's acne flared. Photos were taken of the patient's face. A physical examination of her face revealed 2+ papules and 2+ pustules.

The second patient was placed on topical 2% cefaclor in accordance with the invention. Her oral ampicillin was continued at 1 gm. per day, and her topical 2% erythromycin was discontinued. Approximately 6 weeks later, the patient subjectively indicated she cleared within 2 weeks of applying 2% cefaclor topically. Physical examination of her face revealed 0 papules and 0 pustules, a complete clearing of her acne. Photos were again taken.

The third patient is a female who had acne vulgaris since age 23. Over the course of 12 years she was treated for acne vulgaris with multiple topicals including tretinoin, benzoyl peroxide, and clindamycin solution. At age 35, she had developed an adult variant of acne vulgaris called perioral dermatitis and was treated with oral minocycline 100 mgm. a day and with topical clindamycin. Over the course of the next four months, her oral minocycline was reduced to 50 mgm. per day, and her topical clindamycin was continued. Then the patient flared. Photos were taken of the patient's face. A physical exam revealed 1+ papules and 1+ pustules.

In accordance with the invention, the third patient was placed on 2% topical cefaclor and continued taking oral minocycline at 50 mgm. per day. Approximately 5 weeks later, the patient subjectively noted she experienced great improvement. The physical examination revealed 0 papules on her right cheek, 0.5+ papules on her left cheek, and 0 pustules. Photos were obtained.

Patient No. 4 is a female who has acne since the age of 11. She was first seen at age 44 by Dr. Robinson. At that time she had acne rosacea, now called rosacea. Her prior medication 4.5 years ago had been topical 2% Erythromycin pads used twice daily. She presented with a significant flare of her rosacea and gave a history of nursing her child and could not go on any oral medications. She also gave a history of an allergy to penicillin and could not receive any of these agents for the treatment of her rosacea. On physical examination on her face, she had 3+ papules and 2+ pustules. The impression at this time was the acne variant, rosacea. Photos were obtained, and the patient was placed on 2% topical cefaclor. Approximately 5 weeks later, the patient returned and indicated there was a significant improvement after the third week of use of the topical cefaclor. On physical examination of her face, there were 1+ papules and 1+pustules. This was a very significant improvement over her initial presentation. Photos were obtained, and the patient was continued on the same regimen.

For convenience, the results of treating the four patients described above are presented in the following "Patient Treatment Table."

| | | | Patient Treatment Table Cephalosporin treating agent: 2% cefaclor in carrier containing water and a water-miscible alcohol. | | |
|---|---|---|---|---|---|
| Patient | Sex | Age of Patient | Baseline Exam of Face | Follow-up Exam of Face | Time between Baseline Exam and Follow-up Exam |
| 1 | F | 23 | 2+ papules<br>2+ comedones | 1+ papules<br>1+ comedones | 5 weeks |
| 2 | F | 30 | 2+ papules<br>2+ pustules | 0 papules<br>0 pustules | 6 weeks |
| 3 | F | 35 | 1+ papules<br>1+ pustules | 0.5+ papules<br>0 pustules | 5 weeks |
| 4 | F | 44 | 3+ papules<br>2+ pustules | 1+ papules<br>1+ pustules | 5 weeks |

In general, in accordance with the present invention, a 2% cephalosporin composition can be prepared in the vehicle "Neutrogina Vehicle N (mild)" such that the overall composition of the 2% cephalosporin composition contains approximately: cephalosporin (2% by weight); ethyl alcohol (41.5% by weight); laureth-4 (0.5% by weight); isopropyl alcohol (6.0% by weight); and purified water (50.0% by weight). The above-described 2% cephalosporin composition is used for the topical treatment of acne in patients in the manner described above for treating patients using 2% cefaclor in "Neutrogina Vehicle N (mild)". More specifically, the cephalosporin antibiotic that is used for topical treatment of acne in patients using the vehicle "Neutrogina Vehicle N (mild)" may be selected from the group consisting of cefaclor; cefadroxil; cefamandole nafate; cefazolin; cefixime; cefmetazole; cefonicid; cefoperazone; ceforanide; cefotanme; cefotaxime; cefotetan; cefoxitin; cefpodoxime proxetil; ceftazidime; ceftizoxime; ceftriaxone; ceftriaxone moxalactam (a 1-oxa-beta-lactam); cefuroxime; cephalexin; cephalosporin C; cephalosporin C, sodium salt; cephalothin; cephalothin, sodium salt; cephapirin; cephradine; the 1-acetyloxy ethyl ester of cefuroxime (cefuroxime-axetil); dihydratecephalothin; moxalactam; and loracarbef.

From the description of the treatment of the patients and the composition examples set forth hereinabove, the weight percent of ethyl alcohol spans 35% to 98.5%. More specifically, the weight percents of ethyl alcohol are as follows: 35.0% in Examples 13 and 30, among other; 41.5% for the treated Patients and in Examples 1, 18, 35, 52, and 69, among others; 48.0% in Examples 7, 24, 41, 58, and 75, among others; 65.0% in Examples 6, 23, 40, 57, and 74, among others; 71.2% in Examples 2, 19, 36, 53, and 70, among others; and 98.5% in Examples 6, 23, 40, 57, and 74, among others.

Similarly, from the description of the treatment of the patients and the composition examples set forth hereinabove, the weight percent of isopropyl alcohol spans 4% to 80%. More specifically, the weight percents of isopropyl alcohol are as follows: 4.0% in Examples 7, 24, 41, 58, and 75, among others; 4.3% in Examples 17, 34, 51, and 68, among others; 6.0% for the treated Patients and in Examples 1, 18, 35, 52, and 69, among others; and 80.0% in Examples 15, 32, 49, and 66, among others.

Similarly, from the description of the treatment of the patients and the composition examples set forth hereinabove, the weight percent of propylene glycol spans 3% to 26.8%. More specifically, the weight percents of propylene glycol are as follows: 3.0% in Examples 3, 20, 37, 54, and 71, among others; 10.0% in Examples 7, 24, 41, 58, and 75, among others; and 26.8% in Examples 2, 19, 36, 53, and 70, among others.

Similarly, from the description of the composition examples set forth hereinabove, the weight percent of glycerin is 6.9% in Examples 17, 34, 51, and 68, among others.

It is well known that the monomeric compounds ethyl alcohol, isopropyl alcohol, propylene glycol, and glycerin are water-miscible alcohols that are pharmaceutically acceptable vehicles that can be applied topically to the skin.

Moreover, a large number of pharmaceutically acceptable polymeric, water-miscible alcohols can also be applied topically to the skin, and these pharmaceutically acceptable polymeric, water-miscible alcohols can also be used as carriers for the cephalosporins.

It is seen in Examples 6, 23, 40, 57, and 74, among others, that the carrier ingredients for the antibiotic can be one water-miscible solvent (ethyl alcohol) without the presence of water.

It is seen in Examples 2, 19, 36, 53, and 70, among others, that the carrier ingredients for the antibiotic can be two water-miscible solvents (ethyl alcohol and propylene glycol) without the presence of water.

It is seen in numerous other Examples that the carrier ingredients for the antibiotic can be two or more water-miscible solvents in the presence of water. The highest weight percent for two or more water-miscible solvents in the presence of water as carriers for the antibiotic can be 99.5% where 0.5% by weight of the respective antibiotic can be present in the composition having 99.5% by weight of the carrier.

From the description of the treatment of the patients and the composition examples set forth hereinabove, the sums of the weight percents of water and water-miscible alcohols selected from the group consisting of ethyl alcohol, isopropyl alcohol, propylene glycol, and glycerin span 42.2% to 99.5%. Thus, the widest range for a water-miscible alcohol either alone, or in combination with another water-miscible alcohol or water, in weight percent, is 42.2% to 99.5%.

Similarly, from the description of the treatment of the patients and the composition examples set forth hereinabove, the sums of the weight percents of the water-miscible alcohols (ethyl alcohol, isopropyl alcohol, propylene glycol, and glycerin) span 11.2% to 90%.

Similarly, from the description of the treatment of the patients and the composition examples set forth hereinabove, the weight percent of water spans 9% to 95%.

It is noted that, compositions containing carrier ingredients, wherein at least one carrier ingredient is selected from the group consisting of water and a water-miscible alcohol, and wherein the combined weight percents of the carrier ingredients is in a range spanning 42.2% to 99.5%, covers lotions, creams, gels, and oil-in-water emulsions.

The foregoing description of the invention has been presented for purposes of illustration and description. It is not intended to be exhaustive or to limit the invention to the precise forms disclosed. Obvious modifications or variations of the methods and compositions of the invention are possible in light of the above teachings. The embodiments were chosen and described in order to best illustrate the principles of the invention and its practical application to thereby enable one of ordinary skill in the art to best utilize the invention in various embodiments and with various modifications as are suited to the particular use contemplated. It is intended that the scope of the invention be defined by the claims appended hereto.

What is claimed is:

1. A method of treating a human being for acne which comprises administering to the human being an amount of a composition consisting essentially of a cephalosporin antibiotic active ingredient selected from the group consisting of cefaclor, cefadroxil, cefamandole nafate, cefazolin, cefixime, cefmetazole, cefonioid, cefoperazone, ceforanide, cefotanme, cefotaxime, cefotetan, cefoxitin, cefpodoxime proxetil, ceftazidime, ceftizoxime, ceftriaxone, ceftriaxone moxalactam (a 1-oxa-beta-lactam), cefuroxime, cephalexin, cephalosporin C, cephalosporin C sodium salt, cephalothin, cephalothin sodium salt, cephapirin, cephradine, the 1-acetyloxy ethyl ester of cefuroxime (cefuroxime-axetil), dihydratecephalothin, moxalactam, and loracarbef and a pharmaceutical carrier, applied directly to affected dermal tissues, effective to treat the acne wherein said pharmaceutical carrier is a mixture of water and a water-miscible alcohol in amounts ranging from 42.2% to 99.5% of the composition.

2. The method described in claim 1 wherein the cephalosporin antibiotic is present in a range of from 0.5% to 10% by weight of the composition.

3. The method described in claim 1 wherein said water-miscible alcohol is ethyl alcohol in a weight percent range spanning 35% to 98.5%.

4. The method described in claim 1 wherein said water-miscible alcohol is isopropyl alcohol in a weight percent range spanning 4% to 80%.

5. The method described in claim 1 wherein said water-miscible alcohol is propylene glycol in a weight percent range spanning 3% to 26.8%.

6. The method described in claim 1 wherein said water is in a weight percent range spanning 9% to 95%.

7. The method described in claim 1 wherein said water-miscible alcohol is in a weight percent range spanning 11.2% to 90%.

8. A method of treating a human being for acne which comprises administering to the human being an amount of a composition consisting essentially of a cephalosporin antibiotic active ingredient selected from the group consisting of cefaclor, cefadroxil, cefamandole nafate, cefazolin, cefixime, cefmetazole, cefonicid, cefoperazone, ceforanide, cefotanme, cefotaxime, cefotetan, cefoxitin, cefpodoxime proxetil, ceftazidime, ceftizoxime, ceftriaxone, ceftriaxone moxalactam (a 1-oxa-beta-lactam), cefuroxime, cephalexin, cephalosporin C, cephalosporin C sodium salt, cephalothin, cephalothin sodium salt, cephapirin, cephradine, the 1-acetyloxy ethyl ester of cefuroxime (cefuroxime-axetil), dihydratecephalothin, moxalactam, and loracarbef, wherein said cephalosporin antibiotic is applied directly to affected dermal tissues in an amount effective to treat the acne, wherein said cephalosporin antibiotic is present in an amount in a range of 0.5–5% by weight and is applied in a carrier consisting essentially of:

ethyl alcohol, in a range of 35–50% by weight,
laureth-4, in a range of 0–1% by weight,
isopropyl alcohol, in a range of 0–10% by weight, and
water, in a range of 35–60% by weight.

9. The method described in claim 8 wherein said cephalosporin antibiotic is present in an amount of 2% by weight and is applied in a carrier consisting essentially of:

ethyl alcohol, 41.5% by weight,
laureth-4, 0.5% by weight,
isopropyl alcohol, 6% by weight, and
water, 50% by weight.

10. A method of treating a human being for acne which comprises administering to the human being an amount of a composition consisting essentially of a cephalosporin antibiotic active ingredient, which is cefaclor, and a pharmaceutical carrier, applied directly to affected dermal tissues, effective to treat the acne, wherein said pharmaceutical carrier is a mixture of water and a water-miscible alcohol in amounts ranging from 42.2% to 99.5% of the composition.

11. A method of treating a human being for acne which comprises the steps of:

topically administering to affected dermal areas of the human being an amount of at least one conventionally topically applied anti-acne medication selected from the group consisting of benzoyl peroxide, sulfur, resorcinol, salicylic acid, and tretinoin in conventional doses, and topically administering to the affected dermal areas a composition which includes an amount of a cephalosporin antibiotic selected from the group consisting of cefaclor, cefadroxil, cefamandole nafate, cefazolin, cefixime, cefmetazole, cefonicid, cefoperazone, ceforanide, cefotanme, cefotaxime, cefotetan, cefoxitin, cefpodoxime proxetil, ceftazidime, ceftizoxime, ceftriaxone, ceftriaxone moxalactam (a 1-oxa-beta-lactam), cefuroxime, cephalexin, cephalosporin C, cephalosporin C sodium salt, cephalothin, cephalothin sodium salt, cephapirin, cephradine, the 1-acetyloxy ethyl ester of cefuroxime (cefuroxime-axetil), dihydratecephalothin, moxalactam, and loracarbef effective to treat the acne, and a pharmaceutical carrier, wherein said pharmaceutical carrier is a mixture of water and a water-miscible alcohol in amounts ranging from 42.2% to 99.5% of the composition.

12. The method described in claim 11 wherein the antibiotic is present in a range of 0.5% to 10% by weight of the composition.

13. A method of treating a human being for acne which comprises the steps of:

topically administering to affected dermal areas of the human being an amount of at least one conventionally topically administered conventional anti-acne medication selected from the group consisting of benzoyl peroxide and tretinoin in conventional doses, and topically administering to the affected dermal areas an amount of a composition consisting essentially of a cephalosporin antibiotic active ingredient selected from the group consisting of cefaclor, cefadroxil, cefamandole nafate, cefazolin, cefixime, cefmetazole, cefonicid, cefoperazone, ceforanide, cefotanme, cefotaxime, cefotetan, cefoxitin, cefpodoxime proxetil, ceftazidime, ceftizoxime, ceftriaxone, ceftriaxone moxalactam (a 1-oxa-beta-lactam), cefuroxime, cephalexin, cephalosporin C, cephalosporin C sodium salt, cephalothin, cephalothin sodium salt, cephapirin, cephradine, the 1-acetyloxy ethyl ester of cefuroxime (cefuroxime-axetil), dihydratecephalothin, moxalactam, and loracarbef and a pharmaceutical carrier, effective to treat the acne, wherein the antibiotic is present in a range of 0.5% to 10% by weight of the composition, wherein said pharmaceutical carrier is a mixture of water and a water-miscible alcohol in amounts ranging from 42.2% to 99.5% of the composition.

14. The method described in claim 13 wherein the conventional anti-acne medication is benzoyl peroxide which is present in a range spanning 1% to 30% by weight.

* * * * *